United States Patent
Ohno

(10) Patent No.: US 12,118,736 B2
(45) Date of Patent: Oct. 15, 2024

(54) VIEWING DISTANCE ESTIMATION METHOD, VIEWING DISTANCE ESTIMATION DEVICE, AND NON-TRANSITORY COMPUTER-READABLE RECORDING MEDIUM RECORDING VIEWING DISTANCE ESTIMATION PROGRAM

(71) Applicants: Swallow Incubate Co., Ltd., Ibaraki (JP); Panasonic Holdings Corporation, Osaka (JP)

(72) Inventor: Toshikazu Ohno, Ibaraki (JP)

(73) Assignees: SWALLOW INCUBATE CO., LTD., Ibaraki (JP); PANASONIC HOLDINGS CORPORATION, Osaka (JP)

( * ) Notice: Subject to any disclaimer, the term of this patent is extended or adjusted under 35 U.S.C. 154(b) by 379 days.

(21) Appl. No.: 17/836,316

(22) Filed: Jun. 9, 2022

(65) Prior Publication Data
US 2022/0301204 A1 Sep. 22, 2022

Related U.S. Application Data

(63) Continuation of application No. PCT/JP2021/021983, filed on Jun. 9, 2021.

(30) Foreign Application Priority Data

Dec. 22, 2020 (JP) .................................. 2020-212617

(51) Int. Cl.
*G06V 40/18* (2022.01)
*G06T 7/536* (2017.01)
(Continued)

(52) U.S. Cl.
CPC ................ *G06T 7/536* (2017.01); *G06T 7/60* (2013.01); *G06T 7/73* (2017.01); *G06V 10/28* (2022.01);
(Continued)

(58) Field of Classification Search
CPC .. G06T 7/536; G06T 7/60; G06T 7/73; G06T 2207/30201; G06V 10/28; G06V 40/18;
(Continued)

(56) References Cited

U.S. PATENT DOCUMENTS

| | | | |
|---|---|---|---|
| 2002/0093515 A1* | 7/2002 | Fay ........................ | G01B 11/14 382/286 |
| 2016/0078680 A1* | 3/2016 | Reif ........................ | G06F 3/011 345/633 |

(Continued)

FOREIGN PATENT DOCUMENTS

| | | |
|---|---|---|
| JP | 2001-145613 | 5/2001 |
| JP | 2004-501463 | 1/2004 |
| JP | 2019-168687 | 10/2019 |

OTHER PUBLICATIONS

International Search Report issued Aug. 24, 2021 in International (PCT) Application No. PCT/JP2021/021983.

*Primary Examiner* — Huy C Ho
(74) *Attorney, Agent, or Firm* — Wenderoth, Lind & Ponack, L.L.P.

(57) ABSTRACT

A viewing distance estimation method includes: acquiring a first image captured by an image capturing device and including a face of a person who watches a target; detecting a size of an iris of the person from the first image; calculating a first value indicating a pixel number for the detected size of the iris; acquiring a resolution of the first image; calculating, based on the first value and a second value indicating a predetermined inherent dimension for the size of the iris, a third value indicating an actual dimension of one pixel;

(Continued)

estimating a viewing distance corresponding to the acquired resolution and the calculated third value, based on relational information representing a relation among the resolution, the third value, and the viewing distance; and outputting estimative information including the estimated viewing distance.

13 Claims, 21 Drawing Sheets

(51) Int. Cl.
    *G06T 7/60*         (2017.01)
    *G06T 7/73*         (2017.01)
    *G06V 10/28*       (2022.01)

(52) U.S. Cl.
    CPC .... *G06V 40/18* (2022.01); *G06T 2207/30201* (2013.01)

(58) Field of Classification Search
    CPC ...... G06V 10/50; G06V 40/161; A61B 3/113; G01B 11/00
    USPC ........................................................ 382/205
    See application file for complete search history.

(56) References Cited

U.S. PATENT DOCUMENTS

| | | |
|---|---|---|
| 2017/0236304 A1* | 8/2017 | Kempinski ............ G06F 3/013 382/117 |
| 2019/0294861 A1 | 9/2019 | Quinteros et al. |
| 2021/0256247 A1 | 8/2021 | Quinteros et al. |

* cited by examiner

VIEWING DISTANCE ESTIMATION METHOD, VIEWING DISTANCE ESTIMATION DEVICE, AND NON-TRANSITORY COMPUTER-READABLE RECORDING MEDIUM RECORDING VIEWING DISTANCE ESTIMATION PROGRAM

TECHNICAL FIELD

This disclosure relates to a technology of detecting a viewing distance between a target and an eye of a person.

BACKGROUND ART

A technology of estimating a distance (viewing distance) between a target watched by a person and an eye of the person serves as an underlying technology applicable to various processes including estimation of a state of the person (e.g., eye fatigue degree). For instance, Patent Literature 1 is known as a technology of estimating a viewing distance. Patent Literature 1 discloses a technology for reducing the likelihood of myopia progression by using a range finder to measure a distance between a user and a display, and automatically disrupting an image displayed on the display when the measured distance falls below a threshold or automatically restoring the image displayed on the image when the measured distance is equal to or longer than the threshold.

Patent Literature 2 discloses a technology of: calculating, based on a pixel number for an iris diameter contained in an image and a known inherent iris dimension which is invariant regardless of a person, an actual dimension of each of pixels; and calculating, based on the calculated actual dimension of each of the pixels and the pixel number for a subject other than the iris contained in the image, an actual dimension of the subject.

However, the technology of Patent Literature 1 requires the dedicated range finder for measuring the viewing distance. Besides, the technology of Patent Literature 2 does not measure the viewing distance. Accordingly, the technologies of Patent Literatures 1 and 2 need to be further improved for achieving such estimation of a viewing distance by a simple structure without providing a range finder.

CITATION LIST

Patent Literature

Patent Literature 1: Japanese Unexamined Patent Publication No. 2019-168687
Patent Literature 2: Japanese Unexamined Patent Publication No. 2004-501463

SUMMARY OF INVENTION

This disclosure has been made to solve the drawbacks described above, and it is an object of this disclosure to provide a technology of estimating a viewing distance by a simple structure without using a range finder.

A viewing distance estimation method according to one aspect of the disclosure is a viewing distance estimation method for a viewing distance estimation device which estimates a viewing distance between a target and an eye of a person. The viewing distance estimation method includes: by a computer included in the viewing distance estimation device, acquiring a first image captured by an image capturing device and including a face of the person who watches the target; detecting a size of an iris of the person from the first image; calculating a first value indicating a pixel number for the detected size of the iris; acquiring a resolution of the first image; calculating, based on the first value and a second value indicating a predetermined inherent dimension for the size of the iris, a third value indicating an actual dimension of one pixel; estimating a viewing distance corresponding to the acquired resolution and the calculated third value, based on relational information representing a relation among the resolution, the third value, and the viewing distance; and outputting estimative information including the estimated viewing di stance.

According to this disclosure, the viewing distance can be estimated by a simpler structure without using a range finder.

DESCRIPTION OF EMBODIMENTS

Circumstances LED Up to this Disclosure

Figure 1:
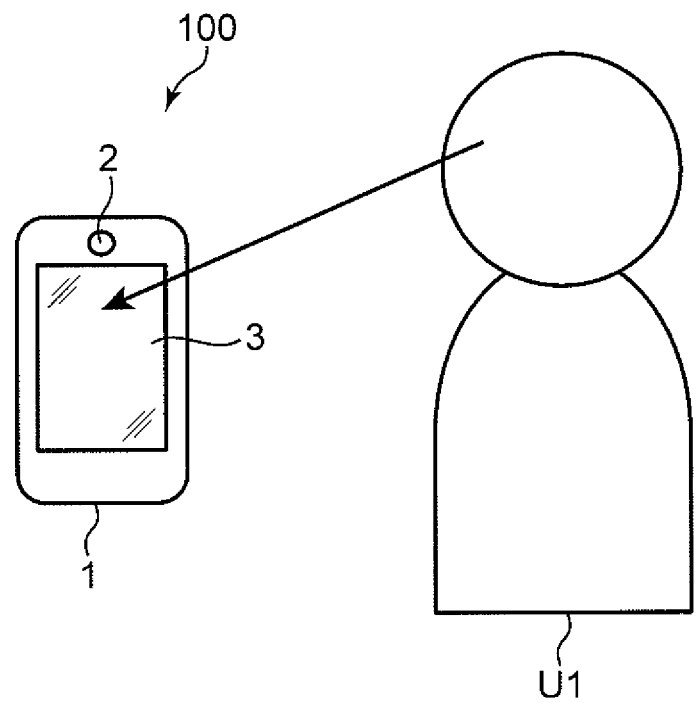
FIG. 1 is an external view of a viewing distance estimation system according to a first embodiment of this disclosure.

Along with the widespread digital equipment, a person has experienced an increase in opportunities of watching or viewing a display of a portable terminal device, such as a smartphone and a tablet device. The increase in the opportunities may induce asthenopia. For instance, asthenopia is avoidable in advance by incorporating, into the portable terminal device, operability of measuring a viewing distance between a display and an eye of the person and warning the person when the eye of the person is too close to the display.

However, Patent Literature 1 uses the range finder, such as an infrared range finder and an ultrasonic transducer emitter, to measure the viewing distance. In this respect, Patent Literature 1 needs to incorporate the range finder into a portable terminal device in advance or externally attach the range finder to the portable terminal device, and thus has a problem of a size-increase and complication in the configuration of the portable terminal device.

Furthermore, Patent Literature 2 utilizes the knowledge that the inherent dimension for the iris diameter is invariant, but it is the subject contained in the image that is targeted for the measurement of an actual dimension thereof without measuring the viewing distance.

Hereinafter, the following operations are focused on: measurement of an actual dimension of one pixel based on a known inherent dimension for an iris diameter and a pixel number for the iris diameter coming into existence in a captured image of a person; and calculation of a viewing distance by utilizing the measured actual dimension of the one pixel.

A resolution of an image varies depending on a kind of an image capturing device or an image capturing mode. For instance, even when a pixel number for an iris is expressed as n-pixels in an image having a resolution of one megapixel, the pixel number for the iris is expressible as 2n-pixels on an image having a resolution of two megapixels. That is to say, the weight per pixel for the known inherent dimension for the iris diameter differs depending on the resolution of the image. Therefore, mere utilization of the actual dimension of the one pixel as calculated based on the known inherent dimension for the iris diameter and the pixel number for the iris diameter results in failing to estimate the viewing distance.

The present inventor having had studied the foregoing in detail obtained the knowledge that a viewing distance can be estimated by a simple structure using the known inherent dimension for a size of an iris, a pixel number for the size of the iris detected from an image, and a resolution of the image without providing a range finder, and finally conceived of the following aspects of this disclosure.

A viewing distance estimation method according to one aspect of the disclosure is a viewing distance estimation method for a viewing distance estimation device which estimates a viewing distance between a target and an eye of a person. The viewing distance estimation method includes: by a computer included in the viewing distance estimation device, acquiring a first image captured by an image capturing device and including a face of the person who watches the target; detecting a size of an iris of the person from the first image; calculating a first value indicating a pixel number for the detected size of the iris; acquiring a resolution of the first image; calculating, based on the first value and a second value indicating a predetermined inherent dimension for the size of the iris, a third value indicating an actual dimension of one pixel; estimating a viewing distance corresponding to the acquired resolution and the calculated third value, based on relational information representing a relation among the resolution, the third value, and the viewing distance; and outputting estimative information including the estimated viewing distance.

According to this configuration, the third value indicating the actual dimension of one pixel is calculated, based on the first value indicating the pixel number for the size of the iris detected from the first image and the second value indicating the inherent dimension for the size of the iris of the person. A viewing distance corresponding to the acquired resolution of the first image and the calculated third value is estimated, based on the relational information representing the relation among the resolution of the image, the third value, and the viewing distance.

In this manner, in the configuration, the viewing distance is estimated by using the third value indicating the actual dimension of the one pixel and the resolution of the image. Consequently, this configuration achieves estimation of the viewing distance by a simple structure without providing a range finder.

In the viewing distance estimation method, the viewing distance estimation device may be a portable terminal device including a camera and a display, the target may be the display, and the first image may be captured by the camera.

According to this configuration, the viewing distance from the person who watches the display of the portable terminal device to the display can be estimated. Therefore, the configuration makes it possible to warn the person when the person is, for example, too close to the display. This succeeds in suppressing the asthenopia of the person.

The viewing distance estimation method may further include: detecting, based on the first image, an orientation of the face; and correcting the viewing distance in accordance with the detected orientation of the face.

The pixel number (first value) for the size of the iris coming into existence in the first image becomes smaller as the orientation of the face deviates away from a forward direction. In this case, an estimated viewing distance is longer than an actual viewing distance. This leads to a failure in accurately estimating the viewing distance. According to the configuration, the viewing distance is corrected in accordance with the orientation of the face, resulting in enhancement of the estimation accuracy of the viewing distance.

In the viewing distance estimation method, in the correction of the viewing distance, the viewing distance may be corrected by multiplying the viewing distance by a correction factor of decreasing the viewing distance as the orientation of the face deviates away from a forward direction.

According to this configuration, the viewing distance is corrected by multiplying the viewing distance by the correction factor of decreasing the viewing distance as the orientation of the face deviates away from the forward direction. Consequently, the viewing distance can be accurately estimated regardless of the orientation of the face.

In the viewing distance estimation method, in the detection of the size of the iris, a second image including an eye region of the person may be generated from the first image. A third image may be generated after the second image is binarized, the third image including pixels each having a gradation value smaller than a threshold and represented by a first luminance and pixels each having a gradation value equal to or larger than the threshold and represented by a second luminance. A fourth image may be generated by replacing a pixel coming into existence in a first luminance area having the first luminance, and having the second luminance and satisfying a predetermined criterion with a pixel having the first luminance, in a third image, and the size of the iris may be detected by using the fourth image.

According to this configuration, the fourth image is generated by replacing the pixel coming into existence in the first luminance area, and having the second luminance and satisfying the predetermined criterion with a pixel having the first luminance in the third image. In this manner, an island-like portion coming into existence in an area corresponding to a colored part of an eye in the first luminance area and having the second luminance is filled with the first luminance. The size of the iris is detected by using the fourth image representing the binary image subjected to the filling. This can result in suppressing an influence of outside light and a background reflected in a cornea, and thus the iris can be accurately detected.

In the viewing distance estimation method, a center position of an iris of each of left and right eyes of the person may be detected in the detection of the size of the iris. The method may further include calculating, based on the detected center position of the iris of each of the left and right eyes of the person and the estimated viewing distance, a convergence angle between the eyes of the person.

According to this configuration, the convergence angle between the eyes is calculated, based on the center position of the iris of each of the left and right eyes and the viewing distance, and therefore, a judgment basis for an eye disease of a person can be provided.

In the viewing distance estimation method, in the calculation of the convergence angle, a middle point representing a center between respective eye inner corners of the left and right eyes of the person may be detected, based on the first image. A first distance from the middle point between the eye inner corners to the center position of the iris of the left eye and a second distance from the middle point between the eye inner corners to the center position of the iris of the right eye may be calculated. A first convergence half-angle may be calculated, based on the first distance and the estimated viewing distance, and a second convergence half-angle may be calculated, based on the second distance and the estimated viewing distance. A sum of the first convergence half-angle and the second convergence half-angle may be calculated as the convergence angle.

According to this configuration, the middle point between the respective eye inner corners of the eyes is detected, based on the first image. The first distance from the middle point between the eye inner corners to the center position of the iris of the left eye and the second distance from the middle point between the eye inner corners to the center position of the iris of the right eye are calculated. The first convergence half-angle is calculated, based on the first distance and the estimated viewing distance, and the second convergence half-angle is calculated, based on the second distance and the estimated viewing distance. The sum of the first convergence half-angle and the second convergence half-angle is calculated as the convergence angle. Accordingly, the convergence angle is accurately calculatable.

The viewing distance estimation method may further include displaying the estimative information by superimposing the estimative information on the first image.

According to this configuration, the estimative information including the estimated viewing distance is superimposed on the first image including the face of the person, and thus the estimative information can be displayed on the first image in real time.

In the viewing distance estimation method, the estimative information superimposed on the first image for displaying may include a gauge object generated, based on the first value and the second value, to represent an actual dimension of a subject in the first image.

According to this configuration, the gauge object is displayed in the first image, and thus the actual dimension of the subject can be represented in the first image.

In the viewing distance estimation method, in the detection of the size of the iris, the size of the iris of each of the left and right eyes may be detected. In the estimation of the viewing distance, determination as to whether a detection result of the iris for each of the left and right eyes is appropriate may be made, based on the detected size of the iris. The viewing distance may be estimated by using the third value for one of the left and right eyes that is determined to be appropriate.

The iris is occasionally detected with a size smaller than an expected size when the person blinks or outside light and a background are reflected in a cornea. In this case, an estimated viewing distance is longer than an actual viewing distance, and thus estimation accuracy of the viewing distance decreases. According to this configuration, determination as to whether the detection result of the iris for each of the left and right eyes is appropriate is made, based on the size of the iris of each of the left and right eyes, and the viewing distance is estimated by using the third value for one of the left and right eyes that is determined to be appropriate. In this manner, an appropriate viewing distance can be estimated in consideration of detection of a smaller size of the iris than the expected size thereof.

In the viewing distance estimation method, the relational information may include a regression equation whose explanatory variable is each of the resolution and the third value and whose response variable is the viewing distance.

According to this configuration, the viewing distance can be accurately estimated by using the regression equation.

A viewing distance estimation device according to another aspect of the disclosure is a viewing distance estimation device which estimates a viewing distance between a target and an eye of a person. The viewing distance estimation device includes: an image acquisition part which acquires a first image captured by an image capturing device and including a face of the person who watches the target; an iris detection part which detects a size of an iris of the person from the first image; a pixel number calculation part which calculates a first value indicating a pixel number for the detected size of the iris; a resolution acquisition part which acquires a resolution of the first image; an actual dimension calculation part which calculates, based on the first value and a second value indicating a predetermined inherent dimension for the size of the iris, a third value indicating an actual dimension of one pixel; an estimation part which estimates a viewing distance corresponding to the resolution acquired by the resolution acquisition part and the third value calculated by the actual dimension calculation part, based on relational information representing a relation among the resolution, the third value, and the viewing distance; and an output part which outputs estimative information including the viewing distance estimated by the estimation part.

A viewing distance estimation program according to further another aspect of this disclosure is a viewing distance estimation program for causing a computer to serve as a viewing distance estimation device which estimates a viewing distance between a target and an eye of a person. The viewing distance estimation program further causes the computer to serve as: an image acquisition part which acquires a first image captured by an image capturing device and including a face of the person who watches the target; an iris detection part which detects a size of an iris of the person from the first image; a pixel number calculation part which calculates a first value indicating a pixel number for the detected size of the iris; a resolution acquisition part which acquires a resolution of the first image; an actual dimension calculation part which calculates, based on the first value and a second value indicating a predetermined inherent dimension for the size of the iris, a third value indicating an actual dimension of one pixel; an estimation part which estimates a viewing distance corresponding to the resolution acquired by the resolution acquisition part and the third value calculated by the actual dimension calculation part, based on relational information representing a relation among the resolution, the third value, and the viewing distance; and an output part which outputs estimative information including the viewing distance estimated by the estimation part.

The above-described configurations provide the same advantageous operational effects as those described for the viewing distance estimation method.

This disclosure is achievable as a viewing distance estimation system caused to operate by a viewing distance detection program as well. Additionally, it goes without saying that the program is distributable as a non-transitory computer readable storage medium like a CD-ROM, or distributable via a communication network like the Internet.

Each of the embodiments which will be described below represents a specific example of the disclosure. Numeric values, shapes, structural elements, steps, and the order of the steps described below are mere examples, and thus should not be construed to delimit the disclosure. Moreover, structrual elements which are not recited in the independent claims each showing the broadest concept among the structrual elements in the embodiments are described as selectable structrual elements. The respective contents are combinable with each other in all the embodiments.

First Embodiment

FIG. 1 is an external view of a viewing distance estimation system 100 according to a first embodiment of this disclosure. The viewing distance estimation system 100 includes a portable terminal device, such as a smartphone or a tablet device. However, this is a mere example, and hence, the viewing distance estimation system 100 may be configured in appropriate combination with a desktop-type computer or a cloud server, a camera, and a display.

The viewing distance estimation system 100 includes a viewing distance estimation device 1, an image capturing device 2, and a display 3. The viewing distance estimation device 1 estimates a viewing distance between an eye of a person U1 whose image is captured by the image capturing device 2 and the display 3.

The image capturing device 2 includes a camera mounted on the portable terminal device. The image capturing device 2 includes the camera which can capture a color visible light image at a predetermined frame rate.

The display 3 is formed of a display device, such as a liquid crystal display device or an organic EL (Electro Luminescence) display device, mounted onto the portable terminal device. The display 3 displays an image of a face of the person U1 captured by the image capturing device 2. Besides, the display 3 displays estimative information including the viewing distance estimated by the viewing distance estimation device 1 by superimposing the estimative information on the image of the face of the person U1.

Figure 2:
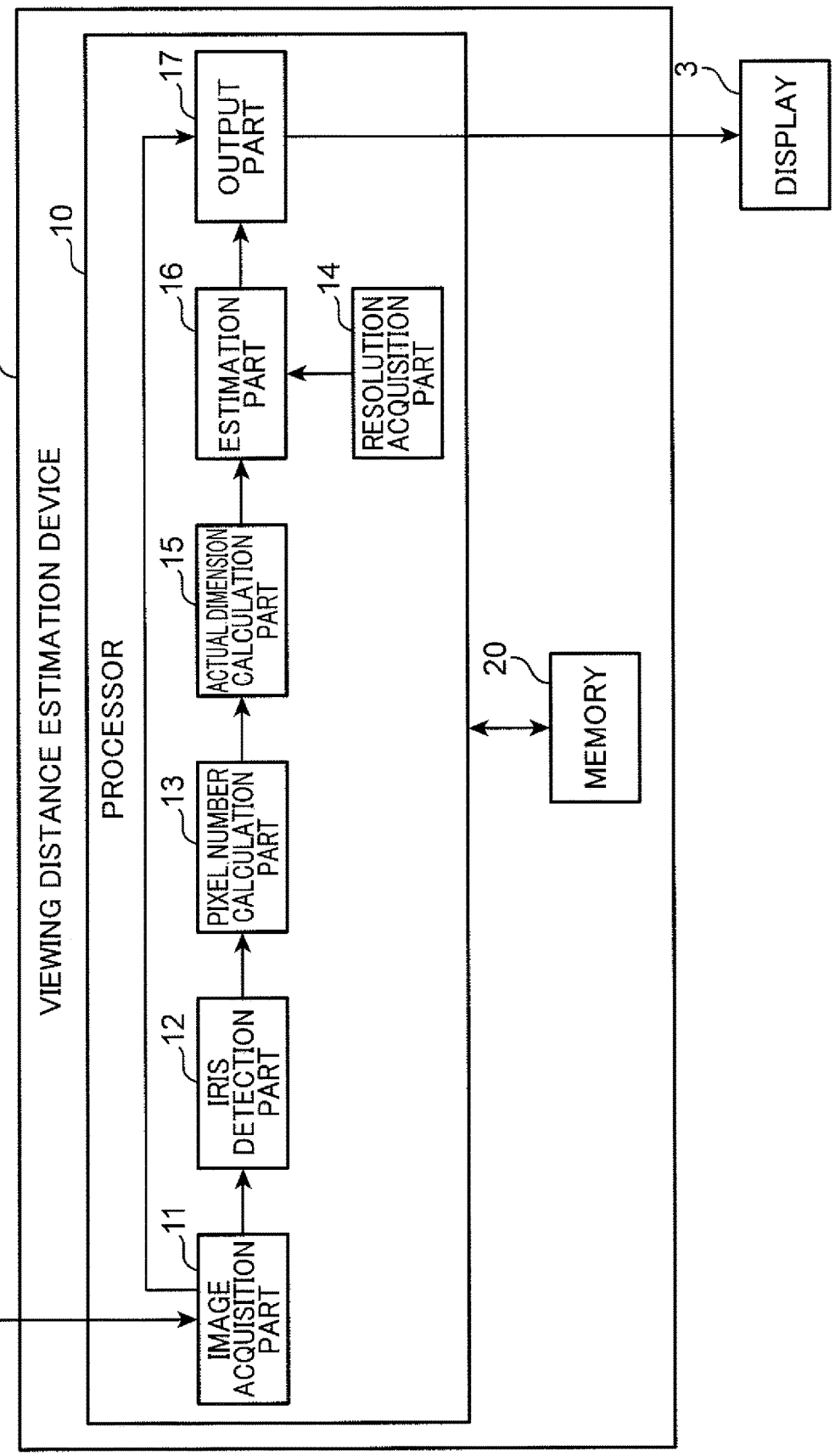
FIG. 2 is a block diagram showing an example of an overall configuration of the viewing distance estimation system according to the first embodiment of this disclosure.

FIG. 2 is a block diagram showing an example of an overall configuration of the viewing distance estimation system 100 according to the first embodiment of this disclosure. The viewing distance estimation device 1 includes a processor 10 and a memory 20. The processor 10 includes, for example, a CPU (Central Processing Unit). The processor 10 includes an image acquisition part 11, an iris detection part 12, a pixel number calculation part 13, a resolution acquisition part 14, an actual dimension calculation part 15, an estimation part 16, and an output part 17. Each of the image acquisition part 11 to the output part 17 comes into effect, for example, when the processor 10 executes a viewing distance estimation program.

The image acquisition part 11 acquires a face image captured by the image capturing device 2 and including a face of a person who watches a target. The target is, for example, the display 3. The image acquisition part 11 sequentially acquires face images captured at a predetermined frame rate. The face image is an example of the first image including the face of the person U1 who watches the target.

The iris detection part 12 detects a size of an iris of the person U1 from the face image acquired by the image acquisition part 11. An iris diameter or an iris radius is adoptable as the size of the iris. In the following description, the iris diameter is referred to as the size of the iris.

Specifically, the iris detection part 12 detects a face region including a region of the face of the person from the face image, and generates an eye detection region (which is an example of the second image) including an eye region of each of left and right eyes of the person U1 from the detected face region. The eye detection region has, for example, a rectangular shape.

Next, the iris detection part 12 generates a binary image (which is an example of the third image) after the eye detection region is binarized, the binary image including pixels each having a gradation value smaller than a threshold and represented by a first luminance and pixels each having a gradation value equal to or larger than the threshold and represented by a second luminance. Here, in a case where the eye detection region is composed of a color image, the iris detection part 12 may convert the eye detection region to a grayscale image having a gradation value of, for example, 0 to 255, and binarize the grayscale image obtained through the conversion. For instance, Otsu's binarization is employable for the binarizing. The first luminance represents, for example, white, and the second luminance represents, for example, black. Specifically, in the embodiment, a binary image where a dark portion is expressed in white and a bright portion is expressed in black is generated. The luminance of white is represented by, for example, 255, and the luminance of black is represented by, for example, 0.

Subsequently, the iris detection part 12 executes a filling process of replacing a black pixel coming into existence in a white area (first luminance area) having white pixels, and satisfying a predetermined criterion with a white pixel in the binary image. Then, the iris detection part 12 detects the size of the iris by using the binary image subjected to the filling process. In this manner, a binary image where a black island-like portion having come into existence in an area (hereinafter, refer to "colored-part area") corresponding to a colored part of the eye in the white area is filled with white pixels is generated. The binary image subjected to the filling process is an example of the fourth image. The filling process will be described in detail later.

Figure 8:
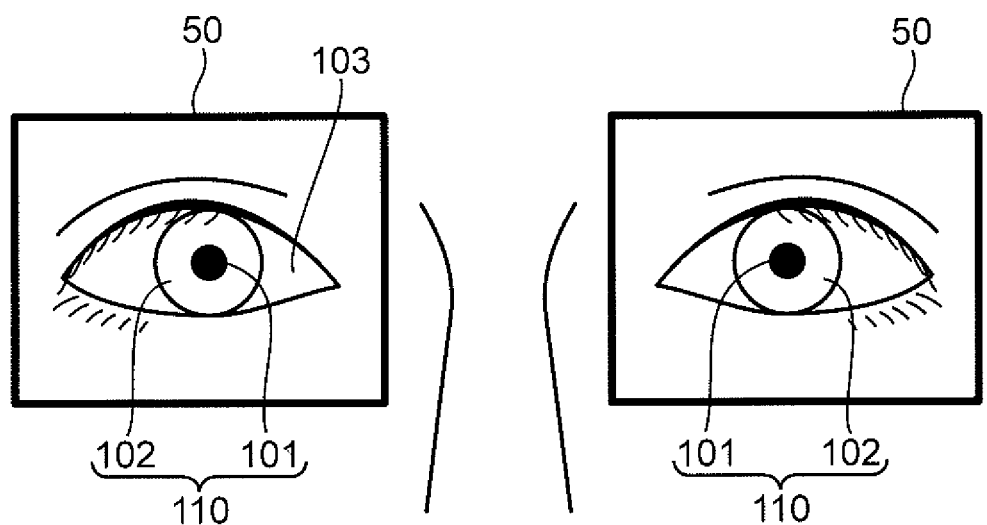
FIG. 8 shows eye detection regions.

Referring to FIG. 8, in the embodiment, the eye includes a white part 103, and a colored part 110 surrounded by the white part 103 and having a circular shape when viewed from the front. The colored part 110 includes a pupil 101 having a circular shape when viewed from the front, and an iris 102 having a donut shape surrounding the pupil 101. In the embodiment, an iris center position, a center position of the colored part 110, and a center position of the pupil 101 agree with one another.

Referring to FIG. 2, the pixel number calculation part 13 calculates a first value indicating a pixel number for the iris diameter detected by the iris detection part 12.

The resolution acquisition part 14 acquires a resolution of the face image. Here, the resolution acquisition part 14 may acquire, as the resolution of the face image, a resolution of the display 3 stored in the memory 20 in advance. Alternatively, the resolution acquisition part 14 may acquire the resolution of the face image by acquiring, from the image capturing device 2, a resolution corresponding to a capturing mode adopted when the image capturing device 2 captures the face image. Further alternatively, the resolution acquisition part 14 may acquire the resolution of the face image by counting the pixel number of the face image acquired by the image acquisition part 11. The acquired resolution may include, for example, a horizontal resolution, or may include a horizontal resolution and a vertical resolution.

The actual dimension calculation part 15 calculates, based on the first value calculated by the pixel number calculation part 13 and a second value indicating a predetermined inherent dimension for the iris diameter, a third value indicating an actual dimension of one pixel. The inherent dimension for the iris diameter means an inherent dimension of the iris diameter that is invariant regardless of the person U1, and represents a known value. Examples of the second value include a value of around 12 mm. In use of an iris radius as the size of the iris, an inherent dimension for the iris radius is adopted as the second value.

The estimation part 16 estimates a viewing distance corresponding to the resolution acquired by the resolution acquisition part 14 and the third value calculated by the actual dimension calculation part 15, based on relational information representing a relation among the resolution, the third value, and the viewing distance.

The relational information includes a regression equation whose explanatory variable is each of the resolution and the third value and whose response variable is the viewing distance, the regression equation being established in advance through regression analysis of, for example, a plurality of datasets where a resolution, a third value, and a viewing distance are associated with one another. Alternatively, the relational information may include a machine learning model defining the viewing distance as an output, and each of the resolution and the third value as an input, the machine learning model being established by learning a plurality of datasets through machine learning, such as a neutral network.

The datasets are acquired by the following actual measurement. For instance, a distance between the image capturing device 2 having a specific resolution and the person U1 is changed by the image capturing device 2, and simultaneously, the pixel number for the iris diameter is measured per distance. Subsequently, an inherent dimension (e.g., 12 mm) for the iris diameter is divided by the measured pixel number for the iris diameter to obtain the third value. Such calculation to obtain the third value is executed many times while changing the resolution. Consequently, the datasets where the resolution, the third value, and the viewing distance are associated with one another are obtainable.

The output part 17 outputs estimative information including the viewing distance estimated by the estimation part 16.

The memory 20 includes, for example, a non-volatile storage device, and stores the relational information.

Figure 3:
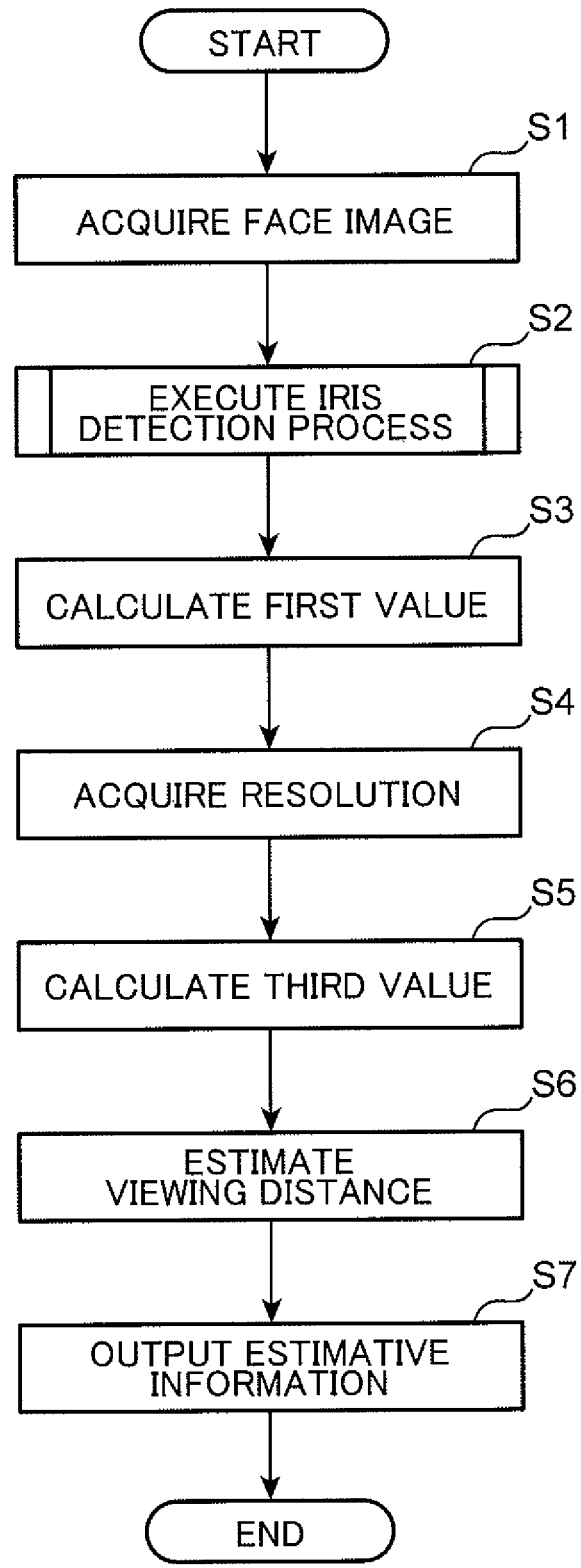
FIG. 3 is a flowchart showing an exemplary process by a viewing distance estimation device according to the first embodiment of this disclosure.

Next, a process by the viewing distance estimation device 1 will be described. FIG. 3 is a flowchart showing an exemplary process by the viewing distance estimation device 1 according to the first embodiment of this disclosure. The flow shown in the flowchart in FIG. 3 is executed in a predetermined sampling period. The predetermined sampling period includes, for example, a frame period of the image capturing device 2.

In step S1, the image acquisition part 11 acquires a face image from the image capturing device 2. In step S2, the iris detection part 12 executes an iris detection process to detect an iris diameter of the person U1 contained in the face image. Here, the iris detection part 12 detects the iris diameter of each of left and right eyes of the person U1. However, this is just an example, and the iris detection part 12 may detect the iris diameter of one of the left and right eyes. The iris detection process will be described in detail later with reference to the flowchart shown in FIG. 4.

Figure 5:
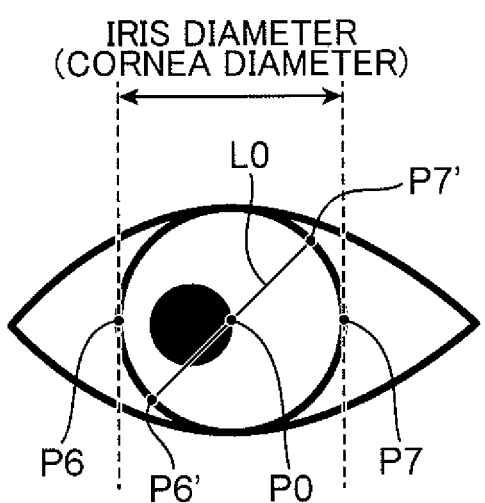
FIG. 5 is an explanatory view for an iris diameter.

In step S3, the pixel number calculation part 13 calculates a first value by counting a pixel number for the iris diameter detected by the iris detection part 12. Here, the pixel number calculation part 13 may calculate the first value by counting the pixel number for the iris diameter of each of the left and right eyes. FIG. 5 is an explanatory view for the iris diameter. In the iris detection process, a left end pixel P6 of the iris and a right end pixel P7 of the iris are detected. Thus, the pixel number calculation part 13 may count the pixel number of the face image between the left end pixel P6 and the right end pixel P7, and calculate the obtained pixel value as the first value. For instance, the pixel number calculation part 13 may calculate the first value by counting the pixel number for an X-coordinate located between an X-coordinate of the left end pixel P6 and an X-coordinate of the right end pixel P7. The X-coordinate means a coordinate in an X-direction corresponding to a width direction (horizontal direction) of the face image. The Y-coordinate means a coordinate in a Y-direction corresponding to a longitudinal direction (vertical direction) of the face image.

In this example, a length of the iris in the X-direction is adopted as the iris diameter. This is because the iris diameter in the X-direction is unlikely to be affected by covering with an upper eyelid and blinking, and the length of the iris in the X-direction is generally adopted as the iris diameter. This disclosure is not limited thereto, and a length of the iris in the Y-direction (length between an upper end pixel and a lower end pixel of the colored-part area) may be adopted as the iris diameter. Alternatively, a length between a left end pixel P6' of the iris and a right end pixel P7' of the iris on a diagonal straight line L0 passing through an iris center position P0 may be adopted as the iris diameter.

In step S4, the resolution acquisition part 14 acquires a resolution of the face image. Here, a horizontal resolution of the face image is obtained.

In step S5, the actual dimension calculation part 15 calculates a third value by dividing a second value by the first value. In this manner, the third value indicating an actual dimension of one pixel in the face image is obtainable. Here, the actual dimension calculation part 15 may calculate the third value for each of the left and right eyes.

In step S6, the estimation part 16 estimates a viewing distance by inputting the third value and the resolution into the relational information. Here, the estimation part 16 may input, for example, an average value of the third values of the respective left and right eyes into the relational information.

Alternatively, the estimation part 16 may determine, based on the iris diameter of each of the left and right eyes calculated in the iris detection process, whether the iris diameter of each of the left and right eyes is appropriate, and estimate a viewing distance by using the third value for one of the left and right eyes that is determined to be appropriate. Specifically, when determining that the iris diameters of both the two eyes are appropriate, the estimation part 16 may estimate the viewing distance by inputting an average value of the third values for both the left and right eyes into the relational information. In contrast, when determining that the iris diameter of only one of the eyes is appropriate, the estimation part 16 may estimate the viewing distance by inputting the third value for the one of the eyes that is determined to be appropriate into the relational information. Furthermore, when determinizing that neither of the iris diameters of the two eyes is appropriate, the estimation part 16 may avoid estimating the viewing distance. In this case, the estimation part 16 may input an error signal to the output part 17.

The determination as to whether the iris diameter of each of the left and right eyes is appropriate is made, for example, in the following manner. First, the estimation part 16 calculates a width of a predetermined part of the face contained in the face image. Examples of the predetermined part of the face include a forehead of the face. For instance, the estimation part 16 executes a landmark process of detecting a characteristic point onto the face image, thereby detecting a characteristic point at a left end of the forehead of the face and a characteristic point at a right end thereof. Then, a distance between the left and right characteristic points is calculated as the width of the forehead. Subsequently, the estimation part 16 calculates a diameter reference value by multiplying the width of the forehead by a predetermined coefficient. Then, when the iris diameter detected in the iris detection process is the diameter reference value or smaller, the estimation part 16 may determine that the iris diameter is inappropriate.

In this manner, the viewing distance can be appropriately estimated even when the detected size of the iris is smaller than an expected size due to the blinking by the person or reflection of outside light and a background in a cornea.

In step S7, the output part 17 generates estimative information including the estimated viewing distance, and outputs the estimative information. For instance, the output part 17 may generate a display screen image for displaying the estimative information by superimposing the estimative information on the face image, and cause the display 3 to display the display screen image.

Figure 6:
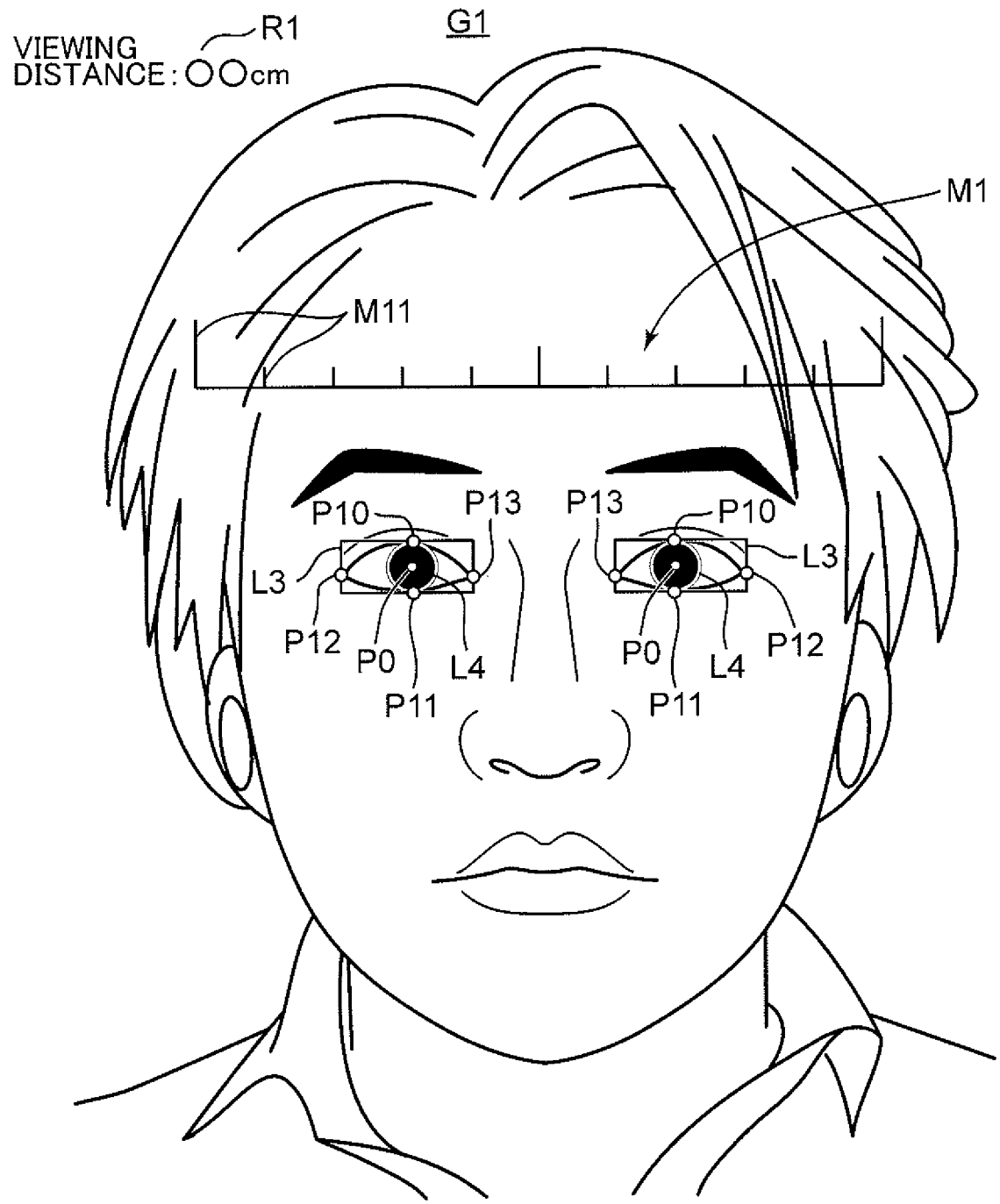
FIG. 6 shows an exemplary display screen image displayed on a display.

FIG. 6 shows an exemplary display screen image G1 displayed on the display 3. The display screen image G1 shows a gauge object M1 above the eyes. The gauge object M1 includes a plurality of scale marks M11. The gauge object M1 indicates an actual dimension of a subject in the face image. The gauge object M1 includes, for example, ten scale marks M11. The interval between the adjacent scale marks M11 corresponds to the actual dimension. In this example, the interval between the scale marks M11 is defined as 1 cm. Therefore, the person U1 seeing the display screen image G1 can understand the actual dimension of a specific part in the face image by using the interval between the scale marks M11. In this example, the width of lips corresponds to around four intervals between the scale marks M11, and hence, the width of the lips is understandable as around 4 cm.

The gauge object M1 is obtained in the following manner. First, the output part 17 obtains a pixel number per unit length by dividing a first pixel by a second pixel. Subsequently, the output part 17 calculates a pixel number for the interval between the scale marks M11 in the face image by multiplying the pixel number per unit length by an actual dimension value (1 cm in this example). Then, the output part 17 may generate the gauge object M1 by arranging the scale marks M11 for each calculated pixel number.

The display screen image G1 includes an upper portion provided with a display section R1 for displaying the viewing distance. In this example, the display section R1 shows 00 cm as the viewing distance. In this way, the person U1 manipulating the portable information terminal device can understand that the viewing distance to the display 3 is ∞ cm.

Here, the output part 17 may determine whether the estimated viewing distance indicates a predetermined viewing distance reference value or smaller, and cause the display screen image G1 to show a warning message when the estimated viewing distance indicates the predetermined viewing distance reference value or smaller.

Additionally, the iris center position P0 is superimposed on the center of the colored part and displayed on the display screen image G1. Besides, an upper eyelid position P10, a lower eyelid position P11, an eye outer corner position P12, and an eye inner corner position P13 are superimposed on the face image of the person U1, and displayed. Moreover, a circle L4 indicating an iris outer edge is superimposed on the face image and displayed. Furthermore, a rectangle L3 passing through the upper eyelid position P10, the eye outer corner position P12, the eye inner corner position P13, and the lower eyelid position P11 is superimposed on the face image, and displayed. For the information about the eye, a result of the iris detection process to be described later is adopted.

Consequently, the display screen image G1 can show, in real time, the information about the eye of the person U1 including the iris information onto the face image captured by the image capturing device 2.

Figure 4:
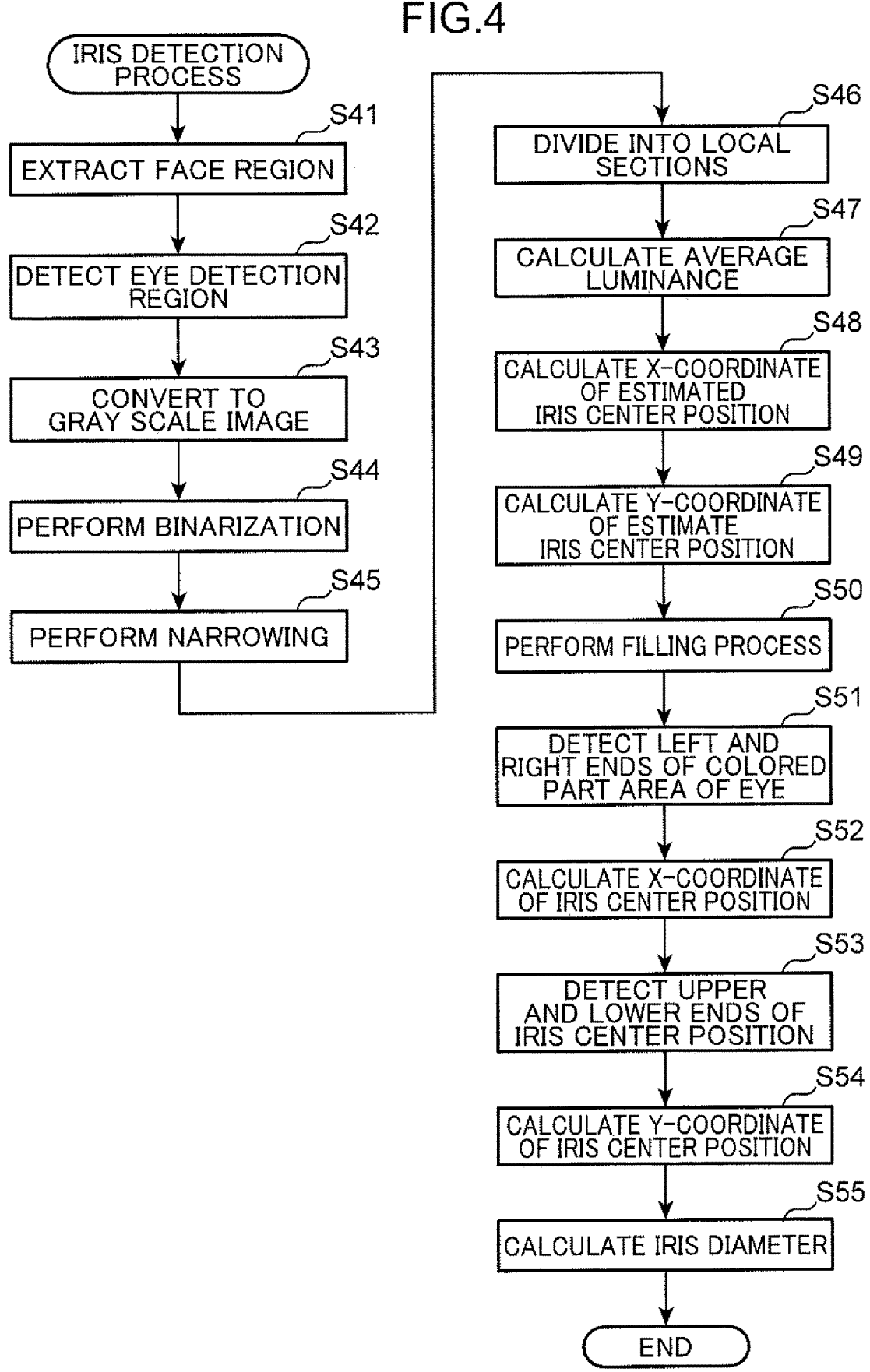
FIG. 4 is a flowchart showing an exemplary iris detection process.
Figure 7:
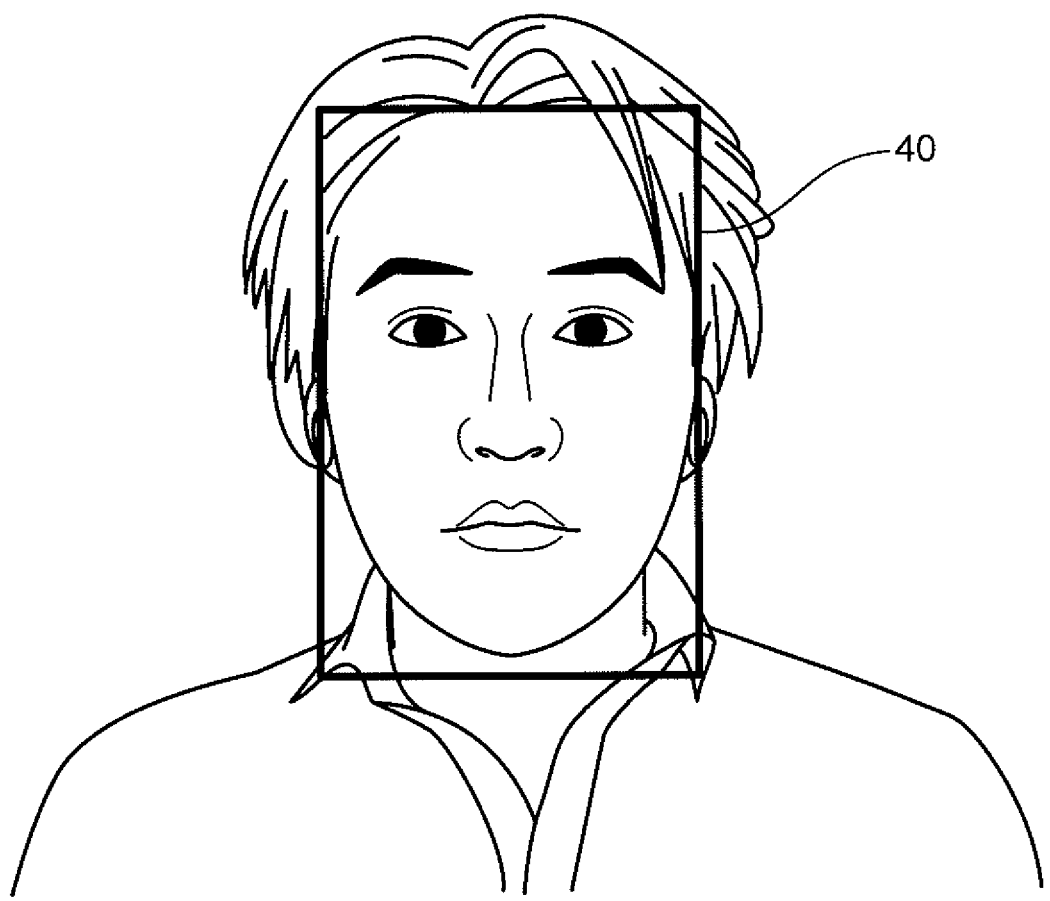
FIG. 7 shows a face region.

Next, the iris detection process will be described in detail. FIG. 4 is a flowchart showing an exemplary iris detection process. In step S41, the iris detection part 12 inputs the face image to a classifier which detects a face region to thereby detect the face region. FIG. 7 shows a face region 40. As shown in FIG. 7, the iris detection part 12 detects, as the face region 40, a rectangular region including an upper portion of the forehead and a lower portion of a chin, and year bases. Here, the face region 40 does not include the entirety of hairs, but may include the entirety of the hairs. FIG. 7 shows the face image obtained by capturing the person U1 from the front thereof, and thus the face image includes both the left and right eyes.

In step S42, the iris detection part 12 inputs the face region 40 detected in step S41 to a classifier which detects an eye detection region to thereby detect the eye detection region. FIG. 8 shows eye detection regions 50. It is seen from FIG. 8 that each of the eye detection regions 50 has a rectangular shape including the whole area of the eye with a some margin in addition to the size of the eye. In FIG. 8, the eye detection regions 50 are extracted respectively for the left and right eyes.

In step S43, the iris detection part 12 convers the eye detection region 50 detected in step S42 to a grayscale image. The conversion to the grayscale image includes, for example, calculating an average gradation value of respective gradation values of a red component, a green component, and a blue component of each of pixels constituting the eye detection region 50. However, this process is just an example, and another process may be adopted for the conversion to the grayscale image.

Figure 9:
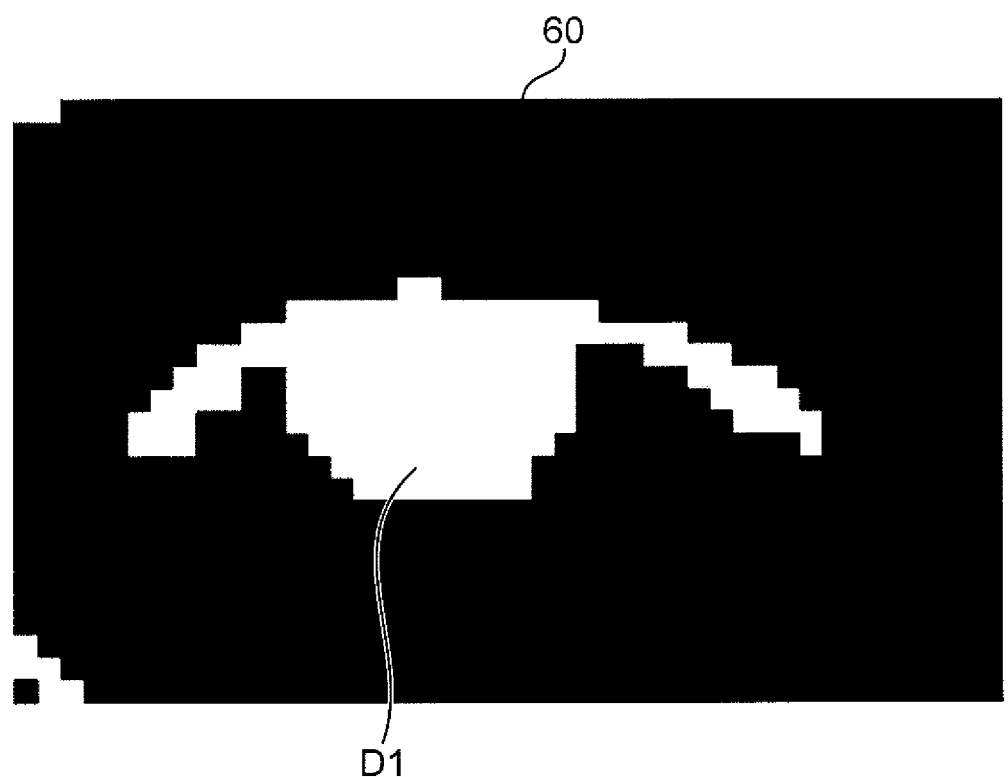
FIG. 9 shows an exemplary binary image.

In step S44, the iris detection part 12 generates a binary image 60 by binarizing the eye detection region 50 converted to the grayscale image. FIG. 9 shows an exemplary binary image 60. In the example shown in FIG. 9, generated is the binary image 60 including the eye detection region 50 where dark parts like the colored part of the eye and eyelashes are expressed in white, and bright parts like the white part of the eye and skin are expressed in black. In the example shown in FIG. 9, the eye information is represented by a mass of white area D1 constituted by white pixels. In the example shown in FIG. 9, no black island-like portion comes into existence in the white area D1 because of less inflection of outside light and a background in a cornea. When such reflection in the cornea occurs, a black island-like portion D2 shown in FIG. 13 comes into existence.

Figure 10:
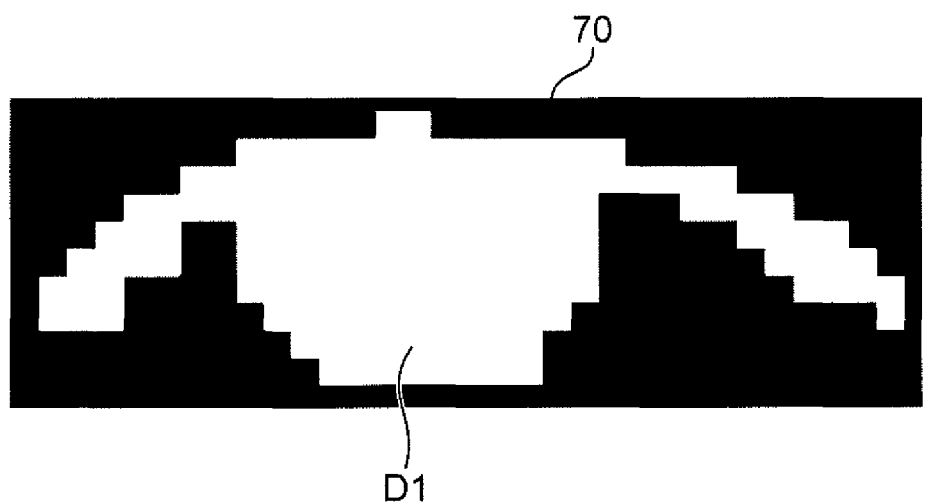
FIG. 10 shows an exemplary binary image subjected to a narrowing process.

In step S45, the iris detection part 12 generates a binary image 70 by applying a narrowing process onto the binary image 60 for removing unnecessary black areas around the white area D1. FIG. 10 shows an exemplary binary image 70 subjected to the narrowing process. In the example shown in FIG. 10, the binary image 70 is generated by setting a bounding rectangle around the white area D1 in the binary image 60 and removing the black areas outside the bounding rectangle. This process succeeds in increasing the accuracy thereafter by removing areas corresponding to a double eyelid, a dark circle under the eye, a mole around the eye, and an eyeglass assembly around the eye.

Figure 11:
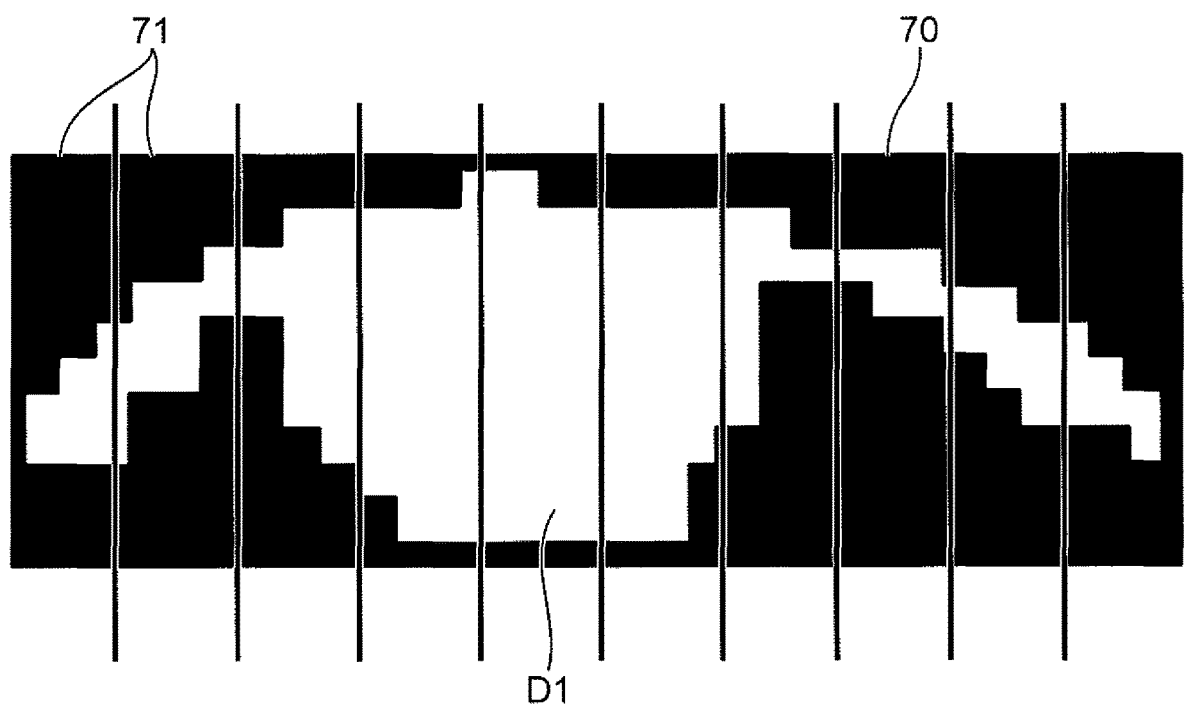
FIG. 11 shows local sections.

In step S46, the iris detection part 12 divides the binary image 70 into a plurality of local sections in the X-direction at predetermined pixels. FIG. 11 shows local sections 71. In the example shown in FIG. 11, the iris detection part 12 divides the binary image 70 equally into ten sections in a width direction. As a result, the binary image 70 is divided into ten local sections 71 each having a strip shape extending in a longitudinal direction thereof corresponding to the Y-reaction. Although the iris detection part 12 divides the binary image 70 into the ten local sections 71, this is just an example. The number of sections may be an integer which is 2 to 9, or 11 or more.

In step S47, the iris detection part 12 calculates an average luminance for the ten local sections 71. Here, the luminance of white is 255, and the luminance of black is 0, and thus, the average luminance is calculated by, for example, the following equation:

Average luminance=the white pixel number for a local section 71×255/the pixel number for the local section 71

Figure 12:
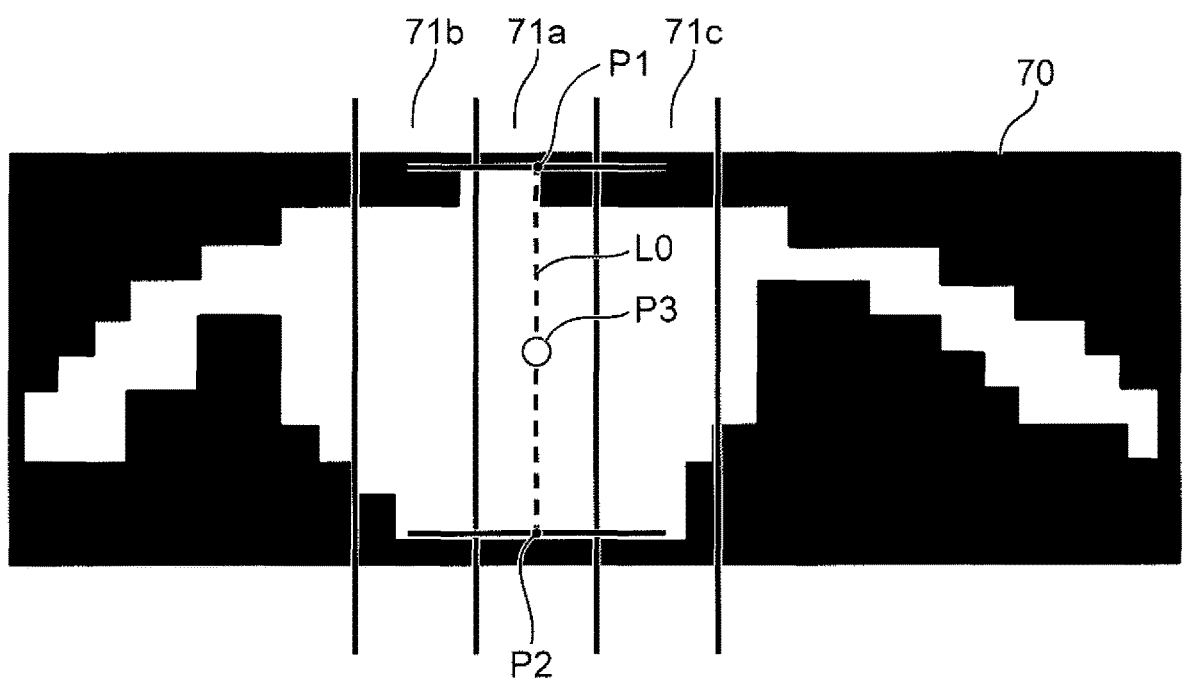
FIG. 12 is an explanatory view for an estimated iris center position.

In step S48, the iris detection part 12 calculates an X-coordinate of an estimated iris center position. FIG. 12 is an explanatory view for an estimated iris center position P3. The estimated iris center position P3 represents an estimated position for the iris center position, and thus differs from the iris center position P0 which is finally calculated. An influence of the double eyelid, a density of the eyelashes, false eyelashes, and the like may be displayed as a large white area D1. In this case, the area corresponding to the white part 103 may be filled with white. Accordingly, the estimated iris center position P3 is calculated to avoid such a situation in this embodiment.

In the example shown in FIG. 12, a fifth local section 71a from the left has a maximum luminance. Hence, the iris detection part 12 calculates a coordinate of a middle point in an X-direction of the local section 71a as the X-coordinate of the estimated iris center position P3. However, the middle point in the X-direction of the local section 71a may not be appropriate as the X-coordinate of the estimated iris center position P3 depending on a width of the local section 71a in the X-direction. In this case, a left end or a right end of the local section 71a in the X-direction may be calculated as the X-coordinate of the estimated iris center position P3.

In step S49, the iris detection part 12 calculates a Y-coordinate of the estimated iris center position P3. Referring to FIG. 12, the iris detection part 12 detects an uppermost end point P1 of the white pixels and a lowermost end point P2 of the white pixels in the local section 71a, and calculates a middle point between the uppermost end point P1 and the lowermost end point P2 as the Y-coordinate of the estimated iris center position P3. The uppermost end point P1 and the lowermost end point P2 may come into existence in a local section 71b adjacent to the left of the aforementioned local section or a local section 71c adjacent to the right of the aforementioned local section due to an influence of the eyelashes and make-up. Accordingly, the iris detection part 12 may calculate an uppermost end point and a lowermost end point for each of the local sections 71a to 71c to obtain an average uppermost end point by averaging the calculated three uppermost end points and calculate an average lowermost end point by averaging the calculated three lowermost end points, thereby calculating a middle point between the average uppermost end point and the average lowermost end point as the Y-coordinate of the estimated iris center position P3.

In step S50, the iris detection part 12 executes a filling process onto the binary image 70. Regarding a visible light image, outside light and a background may reflect in a cornea depending on ambient brightness. When the reflection is much, the colored part which may be in black or brown would have a bright color portion, e.g., a white portion. When the image of the eye is binarized in this state, a black island-like portion comes into existence in the colored-part area, and thus the iris information is undetectable with high accuracy. Therefore, the filling process is executed in the embodiment.

Figure 13:
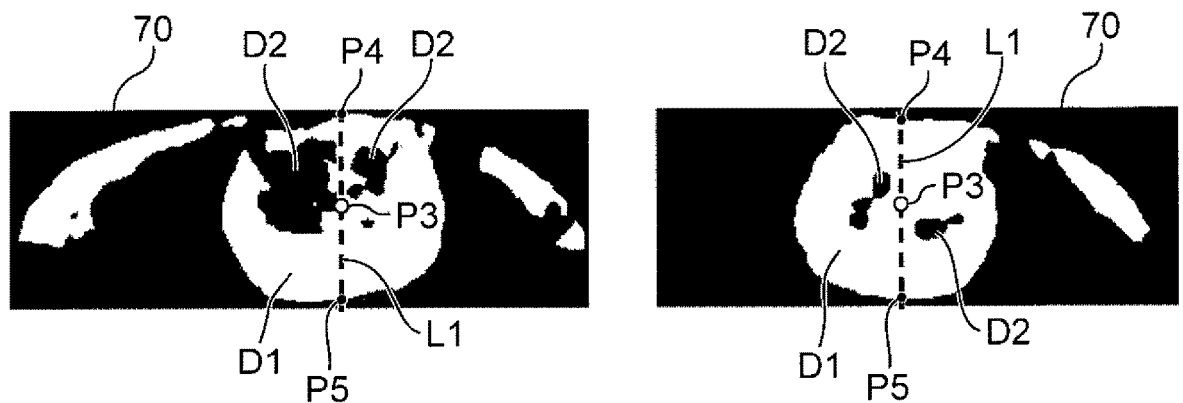
FIG. 13 shows binary images each including black island-like portions coming into existence in a colored-part area.

FIG. 13 shows binary images 70 each including black island-like portions D2 coming into existence in the colored-part area. As shown in FIG. 13, the left view shows the binary image 70 of the left eye, and the right view shows the binary image 70 of the right eye. It is seen from FIG. 13 that the black island-like portions D2 are dotted in the white area D1 corresponding to the colored part appearing at the center in each of the left and right binary images 70. The filling process includes filling the black island-like portions D2. In the description, when the person U1 is seen from the front thereof, the eye located on the left side is defined as the left eye and the eye located on the right side is defined as the right eye. However, this is just an example, and the relation between the eyes may be oppositely defined.

The filling process will be described in detail below. First, the iris detection part 12 sets a vertical line L1 parallel to the Y-direction in the X-coordinate of the estimated iris center position P3 on the binary image 70. Subsequently, the iris detection part 12 detects, as an upper end pixel P4, a white pixel coming into existence first from an upper end of the binary image 70 on the vertical line L1. Then, the iris detection part 12 detects, as a lower end pixel P5, a white pixel coming into existence first from a lower end of the binary image 70 on the vertical line L1. Besides, the iris detection part 12 determines whether a distance between the upper end pixel P4 and the lower end pixel P5 is longer than a first reference distance. Furthermore, the iris detection part 12 determines a black pixel lying between the upper end pixel P4 and the lower end pixel P5 on the vertical line L1 as a black pixel satisfying a predetermined criterion when determining that the distance between the upper end pixel P4 and the lower end pixel P5 is longer than the first reference distance, and converts the black pixel to a white pixel. Conversely, the iris detection part 12 avoids the conversion on the vertical line L1 when determining that the distance between the upper end pixel P4 and the lower end pixel P5 is the first reference distance or shorter. Examples of the first reference distance include a distance suitable for an expected iris diameter.

The iris detection part 12 executes the filling process on each vertical line L1 within a left reference distance range leftward in the X-direction from the estimated iris center position P3 and on each vertical line L1 within a right reference distance range rightward in the X-direction from the estimated iris center position P3. A sum of the left reference distance range and the right reference distance range is defined as a second reference distance. The left reference distance range and the right reference distance range are, for example, the same. Examples of the second reference distance include a distance longer than the expected iris diameter to some extent. In this manner, the filling process is applicable mainly onto the vertical line L1 located in the colored-part area.

Figure 14:
FIG. 14 shows binary images each subjected to a filling process.

FIG. 14 shows binary images 80 each subjected to the filling process. The left view in FIG. 14 shows the binary image 80 obtained by applying the filling process onto the binary image 70 shown in the left view in FIG. 13. The right view in FIG. 14 shows the binary image 80 obtained by applying the filling process onto the binary image 70 shown in the right view in FIG. 13. It is seen from FIG. 14 that the black island-like portions D2 existing in FIG. 13 are filled with white pixels, and a white area D3 constituted by a mass of white pixels is formed. In contrast, it is understood that the black island-like portions corresponding to the eyelashes are not subjected to the filling process. That is to say, the filling process is mainly concentrated on the vertical line L1 located in the colored-part area.

Figure 15:
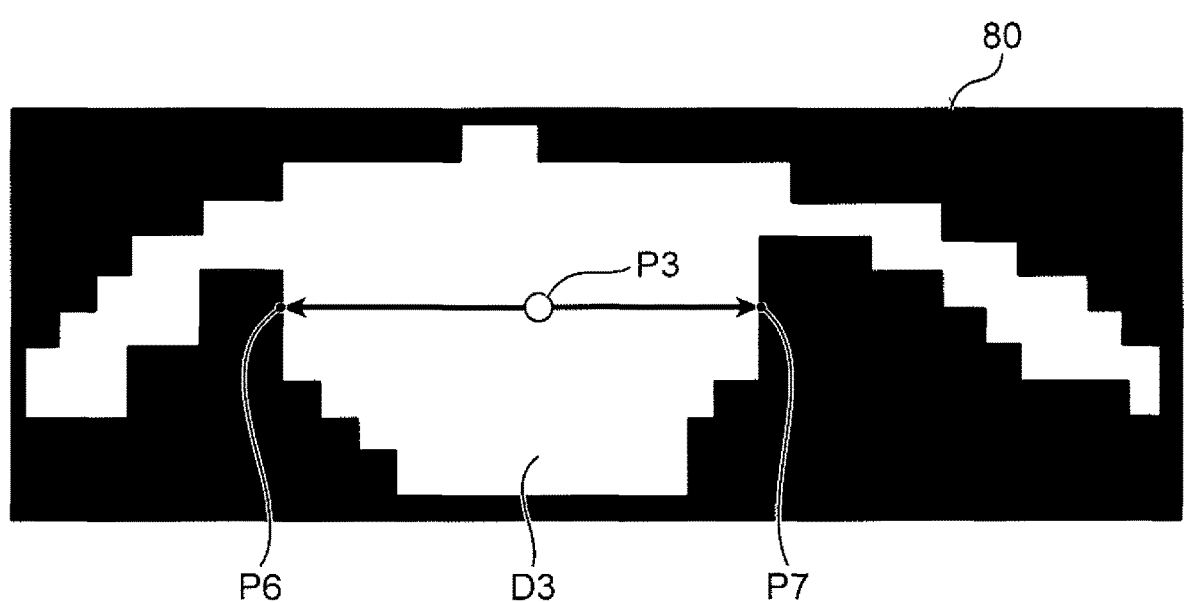
FIG. 15 shows a binary image containing a left end pixel and a right end pixel of the colored-part area which are detected.

In step S51, the iris detection part 12 detects a left end pixel P6 and a right end pixel P7 of the colored-part area. FIG. 15 shows a binary image 80 where the left end pixel P6 and the right end pixel P7 of the colored-part area are detected. The iris detection part 12 examines a change in the luminance of pixels one by one leftward and rightward in the X-direction from the estimated iris center position P3 in the white area D3 of the binary image 80. Then, the iris detection part 12 detects, as the left end pixel P6, a black pixel coming into existence first at a left position in the X-direction, and detects, as the right end pixel P7, a black pixel coming into existence first at a right position in the X-direction.

In step S52, the iris detection part 12 calculate, as an X-coordinate of the iris center position P0, a middle position between the left end pixel P6 and the right end pixel P7.

Figure 16:
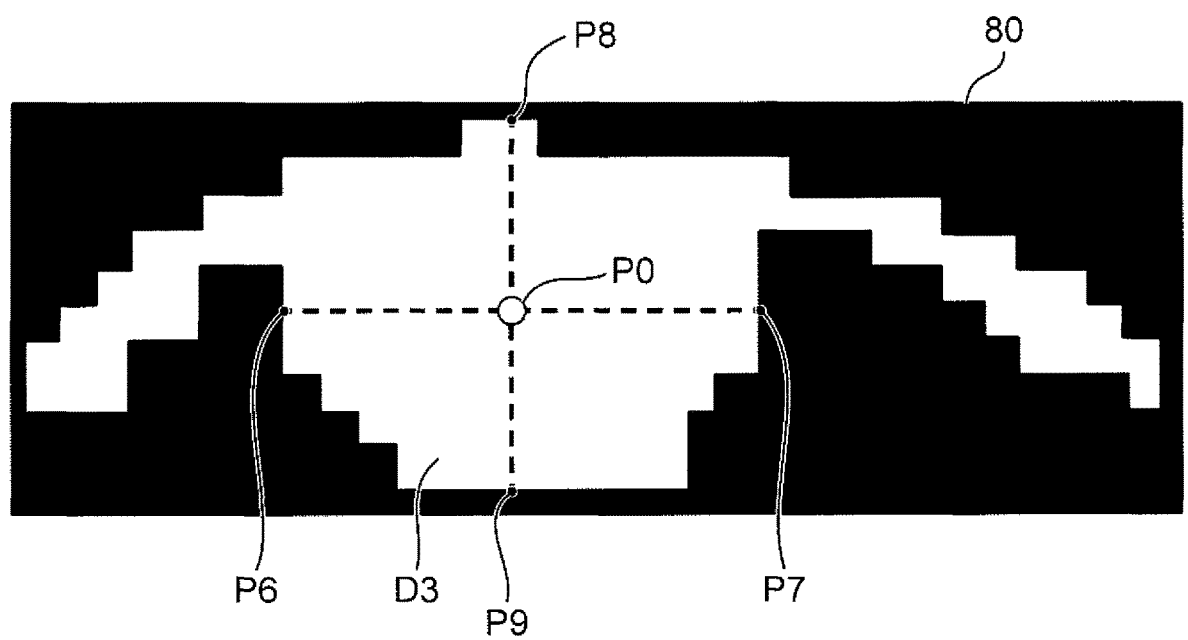
FIG. 16 shows a binary image containing an upper end pixel and a lower end pixel of the colored-part area which are detected.

In step S53, the iris detection part 12 detects an upper end pixel and a lower end pixel of the colored-part area. FIG. 16 shows a binary image 80 where an upper end pixel P8 and a lower end pixel P9 of the colored-part area are detected. The iris detection part 12 examines a change in the luminance of pixels one by one upward and downward in the Y-direction from the iris center position P0 in the white area D3 of the binary image 80. Then, the iris detection part 12 detects, as the upper end pixel P8, a black pixel coming into existence first at an upper position in the Y-direction, and detects, as the lower end pixel P9, a black pixel coming into existence first at a lower position in the Y-direction.

In step S54, the iris detection part 12 calculates, as a Y-coordinate of the iris center position P0, a middle position between the upper end pixel P8 and the lower end pixel P9. Consequently, the iris center position P0 is calculated.

In step S55, the iris detection part 12 calculates, as the iris diameter, a distance between the left end pixel P6 and the right end pixel P7. For instance, the iris detection part 12 may calculate, as the iris diameter, a difference between an X-coordinate of the left end pixel P6 and an X-coordinate of the right end pixel P7.

Besides, the iris detection part 12 may calculate the upper eyelid position P10, the lower eyelid position P11, the eye outer corner position P12, the eye inner corner position P13, the circle L4, and the rectangle L3 each shown in FIG. 6. An upper end pixel at an edge of the white area obtained by executing a morphological gradient calculation to the binary image 80 is adopted as the upper eyelid position P10. A lower end pixel at the edge of the white area obtained by executing the morphological gradient calculation to the binary image 80 is adopted as the lower eyelid position P11. A left end pixel of the white area in the binary image 80 for the left eye is adopted as the eye outer corner position P12 of the left eye. A right end pixel of the white area in the binary image 80 for the left eye is adopted as the eye inner corner position P13 of the left eye. A circle having an iris diameter with a center agreeing with the iris center position P0 is adopted as the circle L4. A rectangle passing through the upper eyelid position P10, the lower eyelid position P11, the eye outer corner position P12, and the eye inner corner position P13 is adopted as the rectangle L3. When the step S55 is finished, the flow proceeds to step S3 in FIG. 3.

Conclusively, in the embodiment, the third value indicating the actual dimension of one pixel is calculated, based on the first value indicating the pixel number for the iris diameter detected from the first image and the second value indicating the inherent dimension of the iris of the person. The viewing distance corresponding to the resolution of the face image and the calculated third value is estimated, based on the relational information representing the relation among the resolution of the image, the third value, and the viewing distance. In this manner, in the embodiment, the viewing distance is estimated by using the third value indicating the actual dimension of the one pixel and the resolution of the face image. Consequently, in the embodiment, the viewing distance can be estimated by a simple structure without providing a range finder.

Second Embodiment

Figure 17:
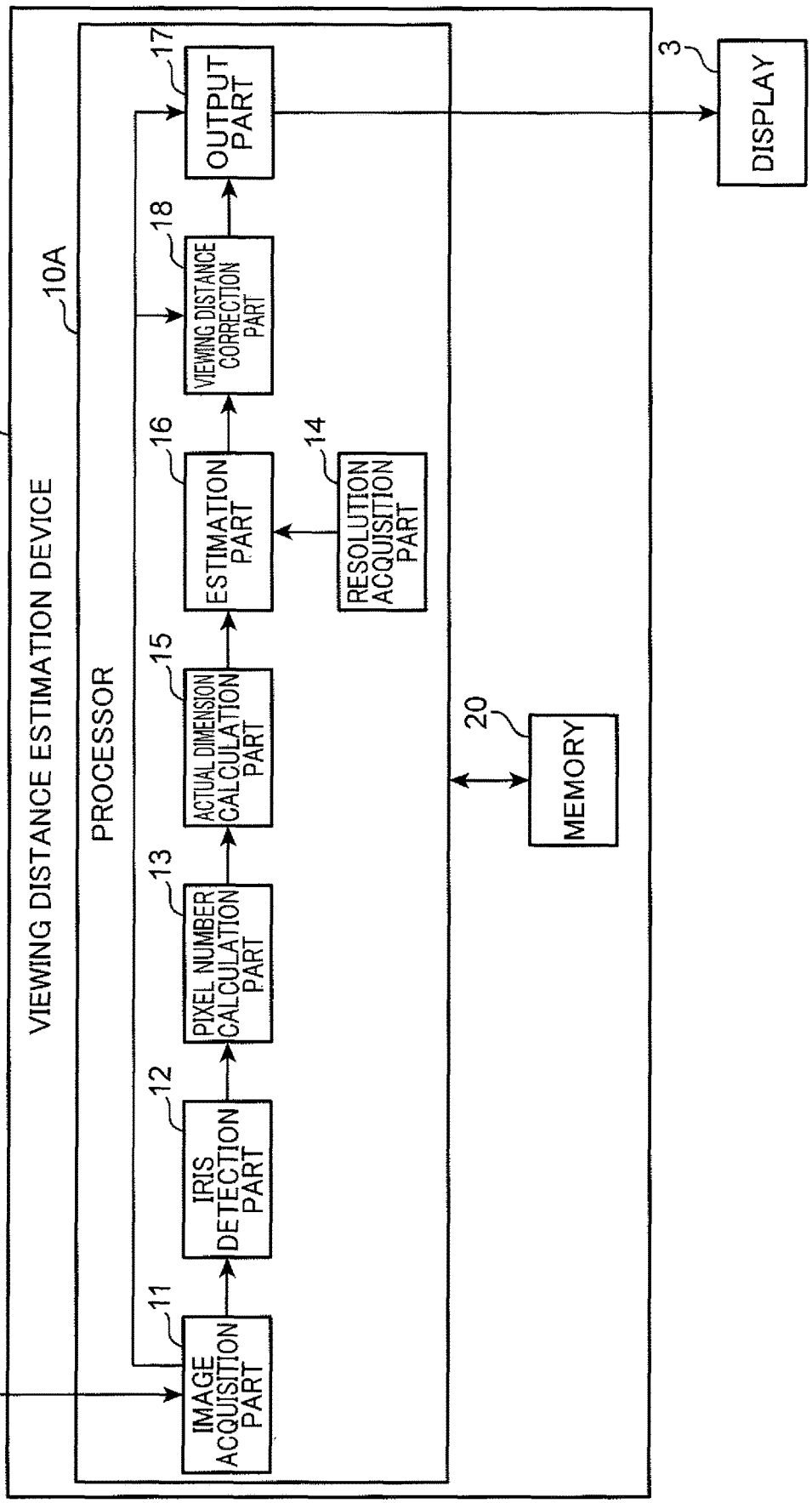
FIG. 17 is a block diagram showing an example of an overall configuration of a viewing distance estimation system according to a second embodiment of this disclosure.

A second embodiment relates to correction of a viewing distance in accordance with an orientation of a face. FIG. 17 is a block diagram showing an example of an overall configuration of a viewing distance estimation system 100 according to the second embodiment of this disclosure. In the embodiment, elements which are the same as those in the first embodiment are given the same reference numerals, and thus explanation therefor will be omitted. The viewing distance estimation system 100 according to the second embodiment includes a viewing distance estimation device 1A. A processor 10A included in the viewing distance estimation device 1A additionally includes a viewing distance correction part 18 in comparison with the processor 10 of the viewing distance estimation device 1.

The viewing distance correction part 18 detects, based on a face image, a face orientation degree indicating a degree of an orientation of a face in a width direction, and corrects a viewing distance estimated by an estimation part 16 in accordance with the detected face orientation degree. In detail, the viewing distance correction part 18 corrects the viewing distance by multiplying the viewing distance by a correction factor of decreasing the viewing distance as the face orientation degree deviates away from a forward direction.

Figure 18:
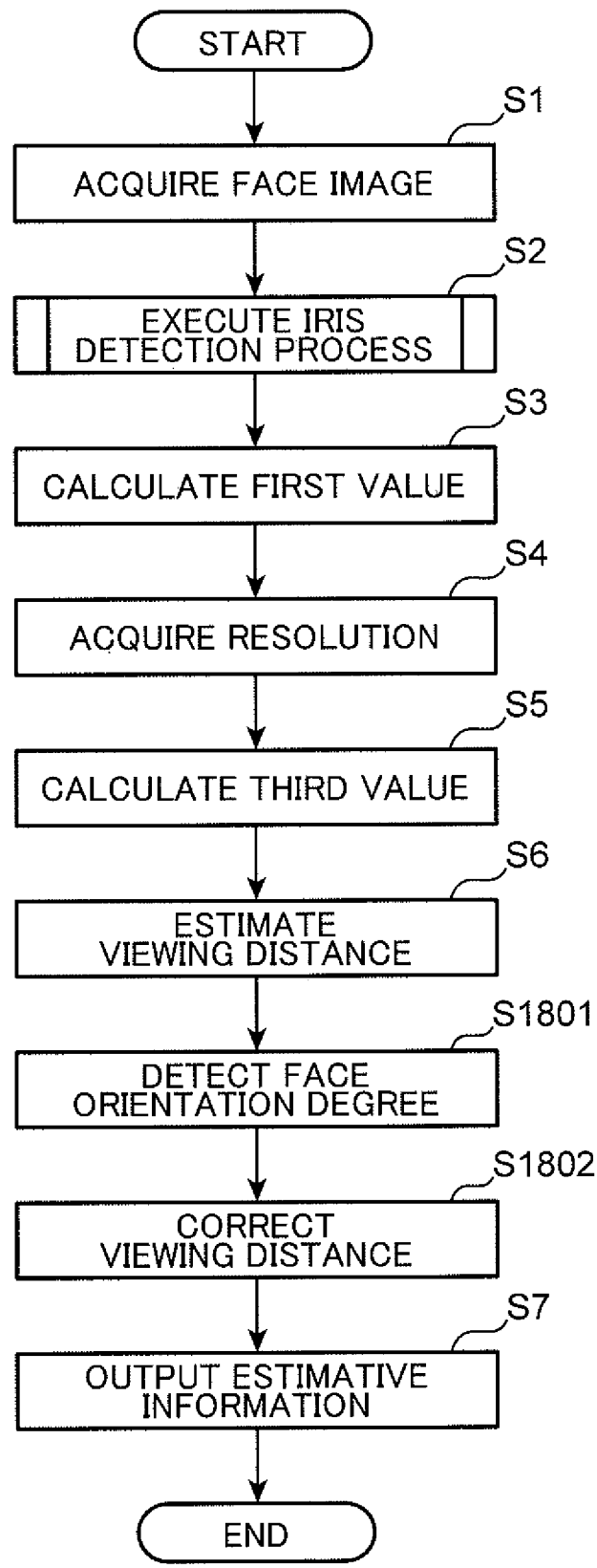
FIG. 18 a flowchart showing an exemplary process by a viewing distance estimation device according to the second embodiment.

FIG. 18 is a flowchart showing an exemplary process by the viewing distance estimation device 1A according to the second embodiment. In the flowchart, steps which are the same as those in FIG. 3 are given the same reference numerals.

Figure 19:
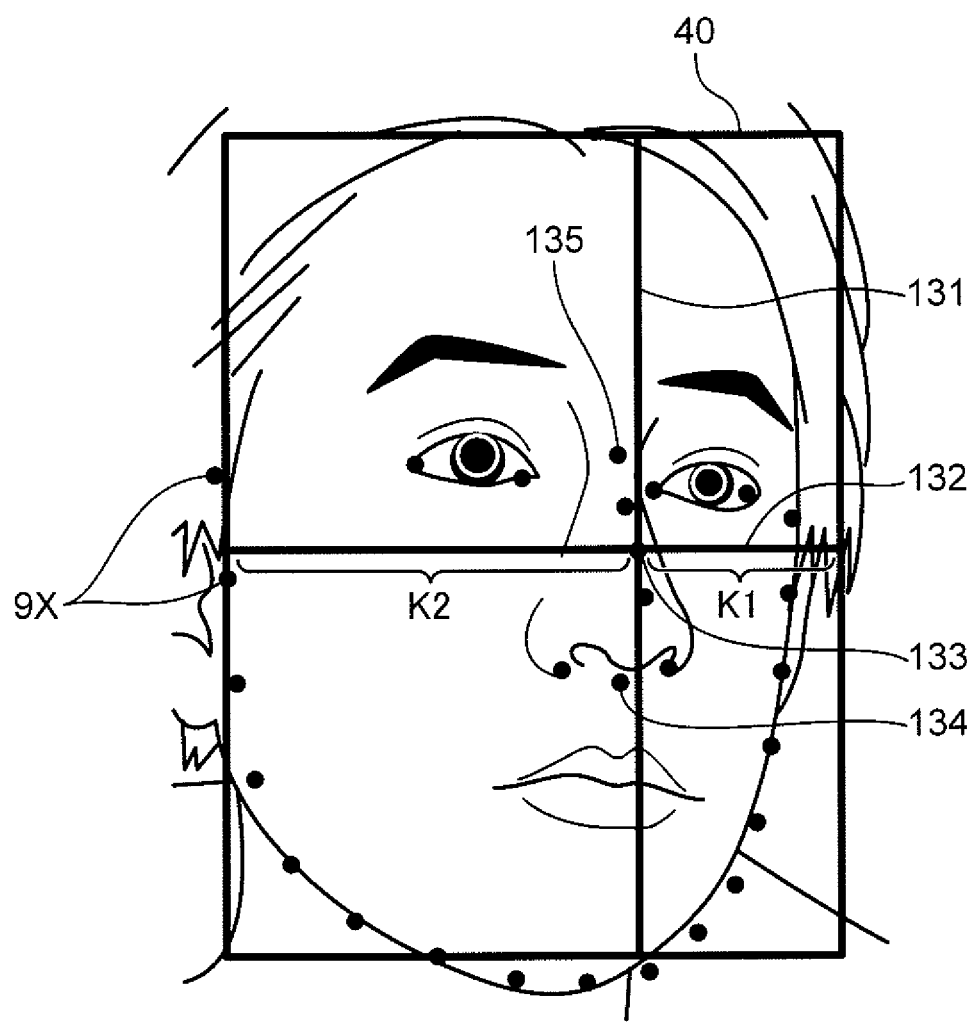
FIG. 19 is an explanatory view for a process of detecting a face orientation degree.

In step S1801 subsequent to step S6, the viewing distance correction part 18 detects, based on a face image, a face orientation degree of a person U1. FIG. 19 is an explanatory view for a process of detecting the face orientation degree.

First, the viewing distance correction part 18 detects a characteristic point by applying a landmark process onto the face image. The characteristic point is called a landmark as well, and indicates a characteristic point of the surface, such as a nose tip, a lip end, and a curve point of a face line.

Subsequently, the viewing distance correction part 18 sets a vertical central line 131 extending in a longitudinal direction and a horizontal central line 132 extending in a width direction, based on characteristic points 9X of the face set in a face region 40. For instance, the viewing distance correction part 18 may set, as the vertical central line 131, a straight line passing through a characteristic point 133 at a center of a nose bridge and extending in parallel to a vertical line of the face region 40. The characteristic point 133 corresponds to, for example, a third characteristic point 9X from above among five characteristic points 9X defining the nose bridge. Then, for instance, the viewing distance correction part 18 sets, as the horizontal central line 132, a straight line passing through the characteristic point 133 and extending in parallel to a side line of the face region 40. Although the vertical central line 131 and the horizontal central line 132 are described to pass through the characteristic point 133 at the center of the nose bridge, but may pass through, for example, a characteristic point 134 at a lower end of the nose bridge or pass through a characteristic point 135 at an upper end of the nose bridge.

Next, the viewing distance correction part 18 divides the horizontal central line 132 at the characteristic point 133 into a right section K1 and a left section K2, and obtains a length of each of the sections. Subsequently, the viewing distance correction part 18 obtains a proportion of each of the right section K1 and the left section K2 when a length of the horizontal central line 132 is defined as 100%, and obtains, based on the proportion, the face orientation degree. The face orientation degree is calculatable by, for example, the formula −(K1−K2) when the proportion of the right section K1 is defined as K1 and the proportion of the left section K2 is defined as K2. In the formula, the sign "−". i.e., minus, at the beginning aims at defining the face orientation degree in facing to the right as a positive value. For instance, in the case of K1=30% and K2=70%, the face orientation degree results in −(30−70)=40. For instance, in the case of K1=70% and K2=30%, the face orientation degree results in −(70−30)=−40. For instance, in the case of K1=50% and K2=50%, the face orientation degree results in −(50−50)=0.

Therefore, the orientation of the face is further rightward as the face orientation degree increases in a positive or plus direction, and the orientation of the face of the face is further leftward as the face orientation degree increases in a negative or minus direction. Moreover, the orientation of the face is in a forward direction when the face orientation degree indicates 0.

In step S1802, the viewing distance correction part 18 refers to correction factor calculation information created in advance, determines a correction factor corresponding to an absolute value of the calculated face orientation degree, and corrects the viewing distance by multiplying the viewing distance estimated in step S6 by the determined correction factor. The correction factor calculation information includes the absolute value of the face orientation degree and the correction factor in association with each other so that the correction factor reduces in a range of 0 to 1 as the absolute value of the face orientation degree increases. For instance, in the correction factor calculation information, the face orientation degree of 0 is associated with the correction factor of 1 indicating the maximum value. The correction factor calculation information further includes the absolute value of the face orientation degree and the correction factor in association with each other so that the correction factor approaches a predetermined lower limit value which is less than 1 as the absolute value of the face orientation degree approaches the maximum value of 50.

In step S7, the estimative information including the corrected viewing distance is output.

A pixel number (first value) for an iris diameter coming into existence in the face image decreases as the orientation of the face deviates away from the forward direction, and accordingly, the estimated viewing distance is longer than an actual viewing distance. This leads to a failure in accurately estimating the viewing distance. According to the configuration, the viewing distance is corrected in accordance with the orientation of the face, resulting in enhancement of the estimation accuracy of the viewing distance.

Third Embodiment

Figure 20:
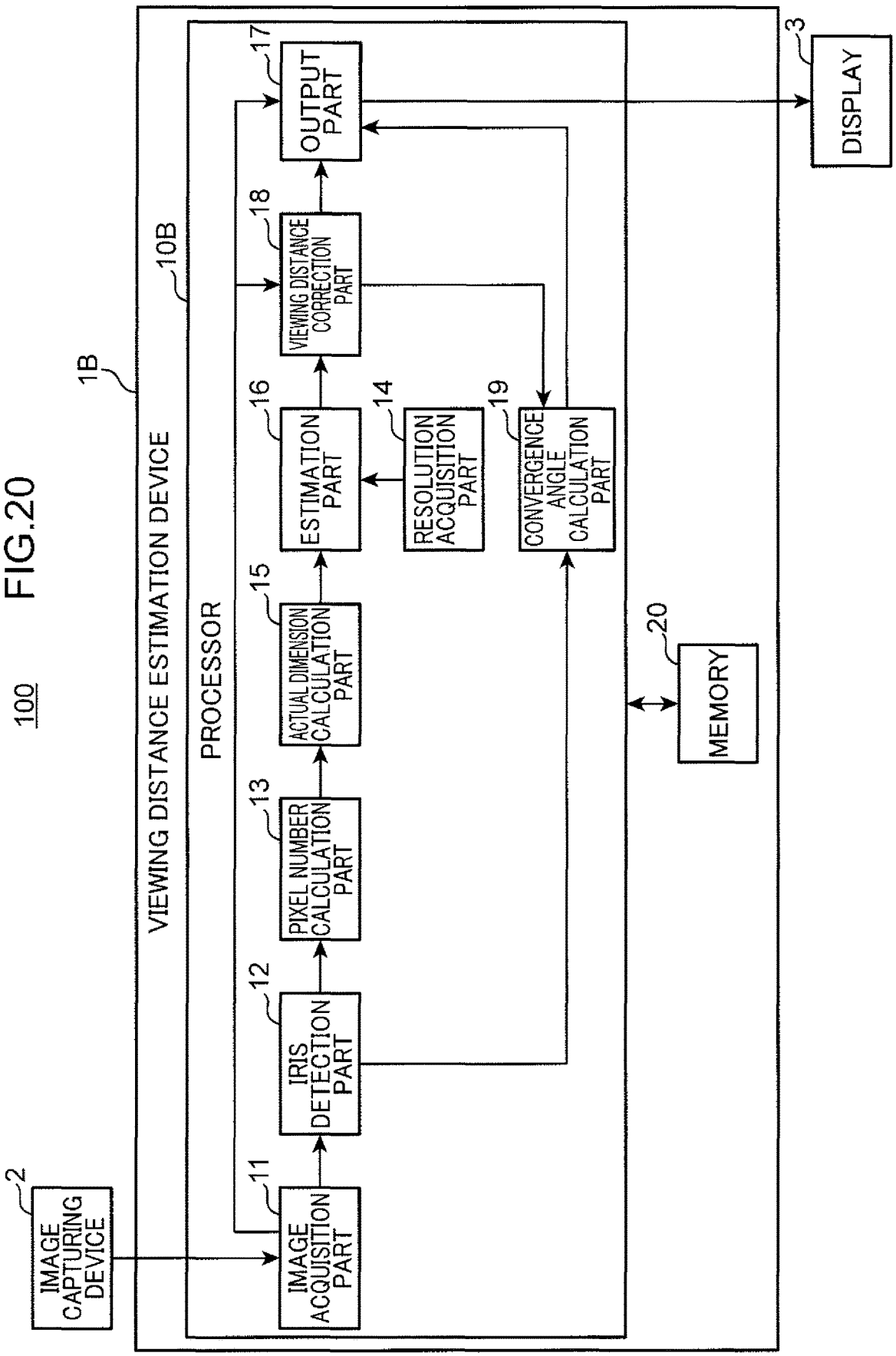
FIG. 20 shows an example of an overall configuration of a viewing distance estimation system according to a third embodiment of this disclosure.

A third embodiment relates to calculation of a convergence angle. The convergence angle is defined between sight lines of both eyes converging at a position of a target being watched. FIG. 20 shows an example of an overall configuration of a viewing distance estimation system 100 according to the third embodiment of this disclosure. In the embodiment, elements which are the same as those in the first and second embodiments are given the same reference numerals, and thus explanation therefor will be omitted. The viewing distance estimation system 100 according to the third embodiment includes a viewing distance estimation device 1B. A processor 10B included in the viewing distance estimation device 1B additionally includes a convergence angle calculation part 19 in comparison with the processor 10A of the viewing distance estimation device 1A.

The convergence angle calculation part 19 calculates, based on an iris center position of an iris of each of left and right eyes of a person U1 as detected by an iris detection part 12 and a viewing distance corrected by a viewing distance correction part 18, a convergence angle between the eyes of the person U1.

Figure 21:
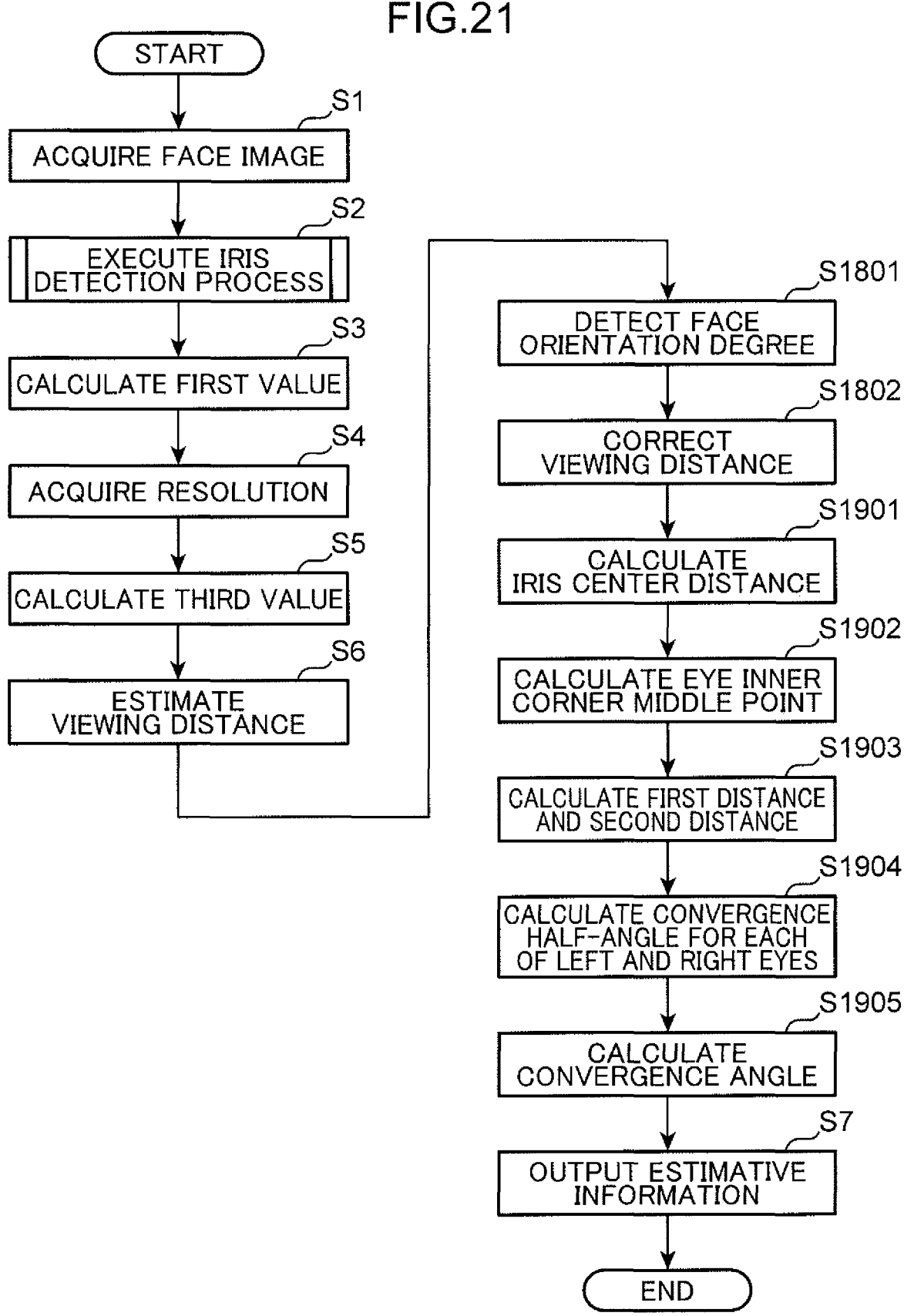
FIG. 21 is a flowchart showing an exemplary process by a viewing distance estimation device according to the third embodiment of this disclosure.
Figure 22:
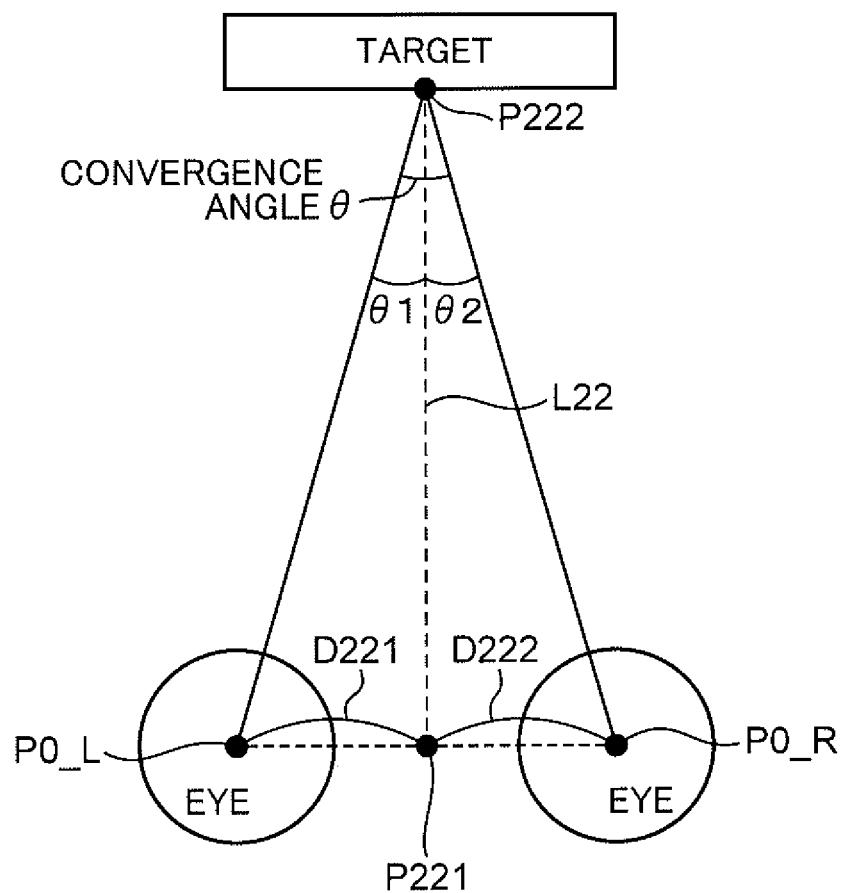
FIG. 22 is an explanatory view for a process of calculating a convergence angle.

FIG. 21 is a flowchart showing an exemplary process by the viewing distance estimation device 1B according to the third embodiment. In the flowchart, steps which are the same as those in FIG. 18 are given the same reference numerals. FIG. 22 is an explanatory view for a process of calculating a convergence angle θ. In step 1901 subsequent to step S1802, the convergence angle calculation part 19 calculates an iris center distance between an iris center position P0_L of the left eye and an iris center position P0_R of the right eye. Here, the iris center position P0 calculated in the iris detection process is utilized as each of the iris center position P0_L and the iris center position P0_R.

In step S1902, the convergence angle calculation part 19 calculates an eye inner corner middle point P221 between an eye inner corner position P13 of the left eye and an eye inner corner position P13 of the right eye. The eye inner corner position P13 detected in the iris detection process is utilized as each of the eye inner corner position P13 of the left eye and the eye inner corner position P13 of the right eye. For instance, the convergence angle calculation part 19 may calculate a difference between X-coordinates of the respective eye inner corner positions P13 of the left and right eyes, and calculate a middle point of the calculated difference as the eye inner corner middle point P221.

In step S1903, the convergence angle calculation part 19 calculates a distance D221 (first distance) between the eye inner corner middle point P221 and the iris center position P0_L, and a distance D222 (second distance) between the eye inner corner middle point P221 and the iris center position P0_R. For instance, the convergence angle calculation part 19 may calculate, as the distance D221, a difference between an X-coordinate of the eye inner corner middle point P221 and an X-coordinate of the iris center position P0_L, and calculate, as the distance D222, a difference between the X-coordinate of the eye inner corner middle point P221 and an X-coordinate of the iris center position P0_R.

In step S1904, the convergence angle calculation part 19 calculates a convergence half-angle θ1 (first convergence half-angle) of the left eye by using a viewing distance L22 and the distance D221, and calculates a convergence half-angle θ2 (second convergence half-angle) by using the viewing distance L22 and the distance D222.

Here, the convergence half-angle θ1 is calculated by arctan (D221/L22) and, the convergence half-angle θ2 is calculated by arctan (d222/22).

In step S1905, the convergence angle calculation part 19 calculates a sum of the convergence half-angle θ1 and the convergence half-angle θ2 as the convergence angle θ.

The calculated convergence angle θ is included in the estimative information and output (step S7). The convergence angle θ may be displayed, for example, on a display screen image G1. In this manner, the convergence angle θ is provided, and therefore a judgment basis for an eye disease can be presented.

This disclosure can adopt modifications described below.

(1) The viewing distance estimation device 1 may include the display 3 and the image capturing device 2 independent of each other. In this case, a viewing distance estimated with relational information results in a viewing distance between the image capturing device 2 and the person U1. Therefore, the estimation part 16 may calculate the viewing distance between the display 3 and the person U1 by correcting the viewing distance estimated with the relational information by using information representing relative positional relation between the display 3 and the image capturing device 2.

(2) Although the face orientation degree is calculated in the image process in the second embodiment, this disclosure is not limited thereto, and a value input by a user using an unillustrated manipulation device (e.g., touch screen) may be adopted as the degree.

(3) The iris detection process described in the first embodiment is just an example, and therefore, this disclosure may adopt another iris detection process. Examples of such iris detection process include a process utilizing, for example, the Doug Leman algorithm.

(4) Although the first luminance represents white and the second luminance represent black in each of the binary images 60, 70, 80 in the first to third embodiment, this disclosure is not limited thereto, and the first luminance may represent black, and the second luminance may represent white.

(5) The relational information may be formed of a lookup table showing a relation among a resolution, a third value, and a viewing distance.

(6) The third embodiment may be applied to the first embodiment. In this case, the convergence angle is not calculated by using a corrected viewing distance, but is calculated by using a viewing distance which is not corrected.

INDUSTRIAL APPLICABILITY

This disclosure achieves estimation of a viewing distance by a simpler structure, and accordingly is useful in technical fields related to the estimation of the viewing distance.

The invention claimed is:

1. A viewing distance estimation method for a viewing distance estimation device which estimates a viewing distance between a target and an eye of a person, comprising:
   by a computer included in the viewing distance estimation device,
   acquiring a first image captured by an image capturing device and including a face of the person who watches the target;
   detecting a size of an iris of the person from the first image;
   calculating a first value indicating a pixel number for the detected size of the iris;
   acquiring a resolution of the first image;
   calculating, based on the first value and a second value indicating a predetermined inherent dimension for the size of the iris, a third value indicating an actual dimension of one pixel;
   estimating a viewing distance corresponding to the acquired resolution and the calculated third value, based on relational information representing a relation among the resolution, the third value, and the viewing distance; and
   outputting estimative information including the estimated viewing distance.

2. The viewing distance estimation method according to claim 1, wherein
   the viewing distance estimation device is a portable terminal device including a camera and a display,
   the target is the display, and
   the first image is captured by the camera.

3. The viewing distance estimation method according to claim 1, further comprising:
   detecting, based on the first image, an orientation of the face; and
   correcting the viewing distance in accordance with the detected orientation of the face.

4. The viewing distance estimation method according to claim 3, wherein,
in the correction of the viewing distance, the viewing distance is corrected by multiplying the viewing distance by a correction factor of decreasing the viewing distance as the orientation of the face deviates away from a forward direction.

5. The viewing distance estimation method according to claim 1, wherein, in the detection of the size of the iris,
a second image including an eye region of the person is generated from the first image,
a third image is generated after the second image is binarized, the third image including pixels each having a gradation value smaller than a threshold and represented by a first luminance and pixels each having a gradation value equal to or larger than the threshold and represented by a second luminance,
a fourth image is generated by replacing a pixel coming into existence in a first luminance area having the first luminance, and having the second luminance and satisfying a predetermined criterion with a pixel having the first luminance in the third image, and
the iris is detected by using the fourth image.

6. The viewing distance estimation method according to claim 1, wherein
a center position of an iris of each of left and right eyes of the person is detected in the detection of the size of the iris,
the method further comprising calculating, based on the detected center position of the iris of each of the left and right eyes of the person and the estimated viewing distance, a convergence angle between the eyes of the person.

7. The viewing distance estimation method according to claim 6, wherein,
in the calculation of the convergence angle,
a middle point representing a center between respective eye inner corners of the left and right eyes of the person is detected, based on the first image,
a first distance from the middle point between the eye inner corners to the center position of the iris of the left eye and a second distance from the middle point between the eye inner corners to the center position of the iris of the right eye are calculated,
a first convergence half-angle is calculated, based on the first distance and the estimated viewing distance, and a second convergence half-angle is calculated, based on the second distance and the estimated viewing distance, and
a sum of the first convergence half-angle and the second convergence half-angle is calculated as the convergence angle.

8. The viewing distance estimation method according to claim 1, further comprising displaying the estimative information by superimposing the estimative information on the first image.

9. The viewing distance estimation method according to claim 1, wherein
the estimative information superimposed on the first image for displaying includes a gauge object generated, based on the first value and the second value, to represent an actual dimension of a subject in the first image.

10. The viewing distance estimation method according to claim 1, wherein, in the detection of the size of the iris, the size of the iris of each of the left and right eyes is detected, and,
in the estimation of the viewing distance, determination as to whether a detection result of the iris for each of the left and right eyes is appropriate is made, based on the detected size of the iris, and the viewing distance is estimated by using the third value for one of the left and right eyes that is determined to be appropriate.

11. The viewing distance estimation method according to claim 1, wherein the relational information includes a regression equation whose explanatory variable is each of the resolution and the third value and whose response variable is the viewing distance.

12. A viewing distance estimation device which estimates a viewing distance between a target and an eye of a person, comprising:
an image acquisition part which acquires a first image captured by an image capturing device and including a face of the person who watches the target;
an iris detection part which detects a size of an iris of the person from the first image;
a pixel number calculation part which calculates a first value indicating a pixel number for the detected size of the iris;
a resolution acquisition part which acquires a resolution of the first image;
an actual dimension calculation part which calculates, based on the first value and a second value indicating a predetermined inherent dimension for the size of the iris, a third value indicating an actual dimension of one pixel;
an estimation part which estimates a viewing distance corresponding to the resolution acquired by the resolution acquisition part and the third value calculated by the actual dimension calculation part, based on relational information representing a relation among the resolution, the third value, and the viewing distance; and
an output part which outputs estimative information including the viewing distance estimated by the estimation part.

13. A non-transitory computer-readable recording medium recording a viewing distance estimation program for causing a computer to serve as a viewing distance estimation device which estimates a viewing distance between a target and an eye of a person, the program further causing the computer to serve as:
an image acquisition part which acquires a first image captured by an image capturing device and including a face of the person who watches the target;
an iris detection part which detects a size of an iris of the person from the first image;
a pixel number calculation part which calculates a first value indicating a pixel number for the detected size of the iris;
a resolution acquisition part which acquires a resolution of the first image;
an actual dimension calculation part which calculates, based on the first value and a second value indicating a predetermined inherent dimension for the size of the iris, a third value indicating an actual dimension of one pixel;
an estimation part which estimates a viewing distance corresponding to the resolution acquired by the resolution acquisition part and the third value calculated by the actual dimension calculation part, based on relational information representing a relation among the resolution, the third value, and the viewing distance; and an output part which outputs estimative information including the viewing distance estimated by the estimation part.

\* \* \* \* \*